(12) United States Patent
Meskens

(10) Patent No.: US 8,626,308 B2
(45) Date of Patent: Jan. 7, 2014

(54) ADJUSTABLE TRANSCUTANEOUS ENERGY TRANSFER SYSTEM

(75) Inventor: Werner Meskens, Opwijk (BE)

(73) Assignee: Cochlear Limited, Macquarie University, NSW (AU)

( * ) Notice: Subject to any disclaimer, the term of this patent is extended or adjusted under 35 U.S.C. 154(b) by 38 days.

(21) Appl. No.: 12/936,356

(22) PCT Filed: Apr. 2, 2009

(86) PCT No.: PCT/US2009/039266
§ 371 (c)(1),
(2), (4) Date: Jan. 3, 2011

(87) PCT Pub. No.: WO2009/124174
PCT Pub. Date: Oct. 8, 2009

(65) Prior Publication Data
US 2011/0106210 A1   May 5, 2011

(30) Foreign Application Priority Data
Apr. 2, 2008 (AU) ................................. 2008901586

(51) Int. Cl.
*A61F 11/04* (2006.01)
(52) U.S. Cl.
USPC .............................................. 607/57; 607/55
(58) Field of Classification Search
USPC .................................................... 607/55–63
See application file for complete search history.

(56) References Cited

U.S. PATENT DOCUMENTS

| 7,856,986 B2 * | 12/2010 | Darley .......................... 128/899 |
| 2004/0012470 A1 | 1/2004 | Zimmerling et al. |
| 2005/0075700 A1 | 4/2005 | Schommer et al. |
| 2005/0159791 A1 | 7/2005 | Daly et al. |
| 2006/0016452 A1 | 1/2006 | Goetz et al. |
| 2006/0030905 A1 * | 2/2006 | Medina Malaver et al ..... 607/61 |
| 2006/0190059 A1 | 8/2006 | Griffith |
| 2006/0271128 A1 | 11/2006 | Keuninckx |
| 2007/0055321 A1 | 3/2007 | Gordon et al. |

FOREIGN PATENT DOCUMENTS

| JP | 10-126286 | 5/1998 |
| JP | 2005-142649 | 6/2005 |
| JP | 58-166110 | 11/2005 |

OTHER PUBLICATIONS

International Preliminary Report on Patentability, PCT/US2009/039266, mailed May 5, 2010.
International Search Report, PCT/US2009/039266, mailed May 26, 2009.
Written Opinion, PCT/US2009/039266, mailed May 26, 2009.
Australian Patent Examination Report for Australian Application No. 2009231721 mailed Feb. 13, 2013 (3 pages).
Office Action for Japanese Patent Application No. 2011-503163 mailed May 28, 2013 along with an English translation (3 pages).

(Continued)

*Primary Examiner* — John Kim
(74) *Attorney, Agent, or Firm* — Kilpatrick, Townsend & Stockton, LLP.

(57) ABSTRACT

A transcutaneous energy transfer system for an implantable medical device. The system comprises an internal coil assembly implantable in a recipient; and an external data coil assembly positioned in a housing worn by the recipient. The data coil assembly is configured to be inductively coupled to the internal coil assembly in order to transcutaneously transfer data to the internal coil assembly. One or more elements of the data coil assembly are physically adjustable with respect to the housing to alter the inductive coupling.

27 Claims, 17 Drawing Sheets

(56) References Cited

OTHER PUBLICATIONS

Office Action for Chinese Patent Application No. 200980115882.3 mailed Mar. 15, 2013 along with an English translation (12 pages).

Extended European Search Report for European Patent Application No. 09728613.2 mailed Sep. 20, 2013 (7 pages).

Office Action for Japanese Patent Application No. 2011-503163 mailed Sep. 17, 2013 along with an English Translation (4 pages).

* cited by examiner

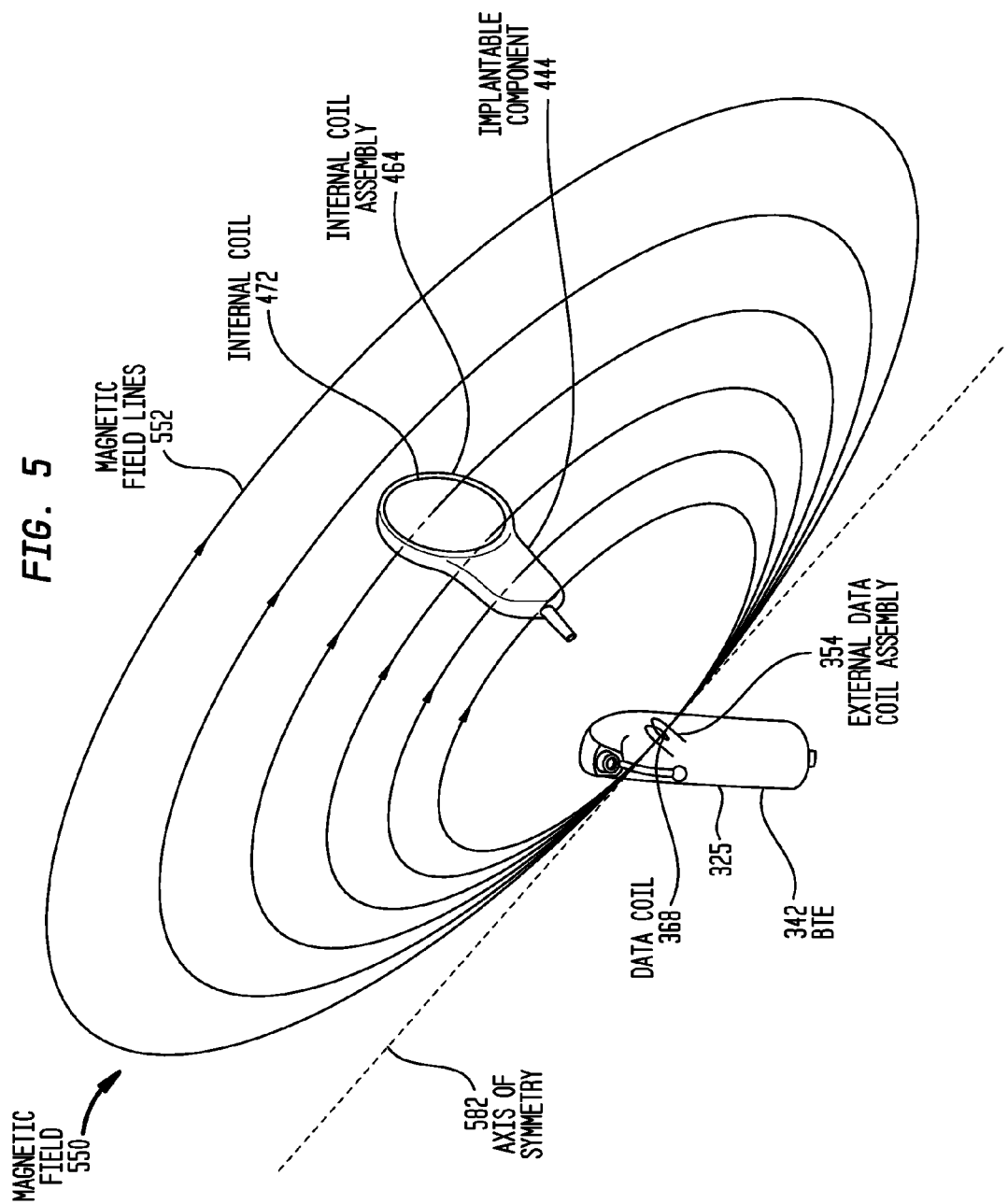

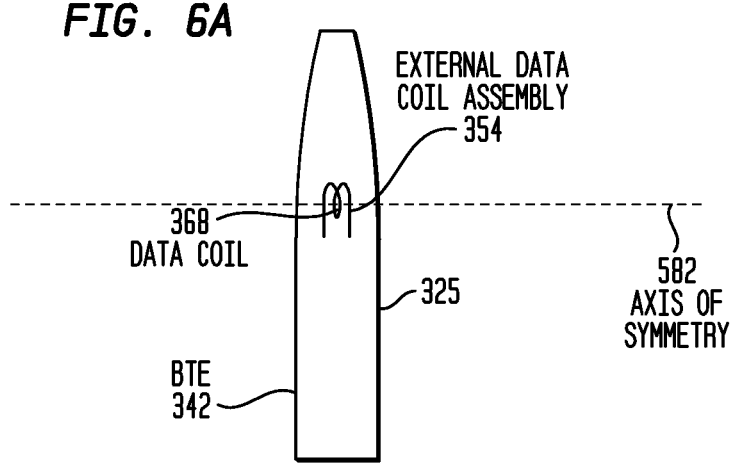
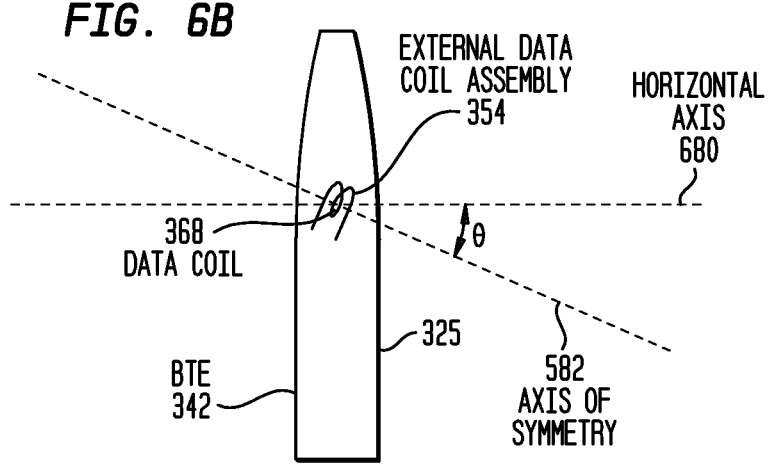
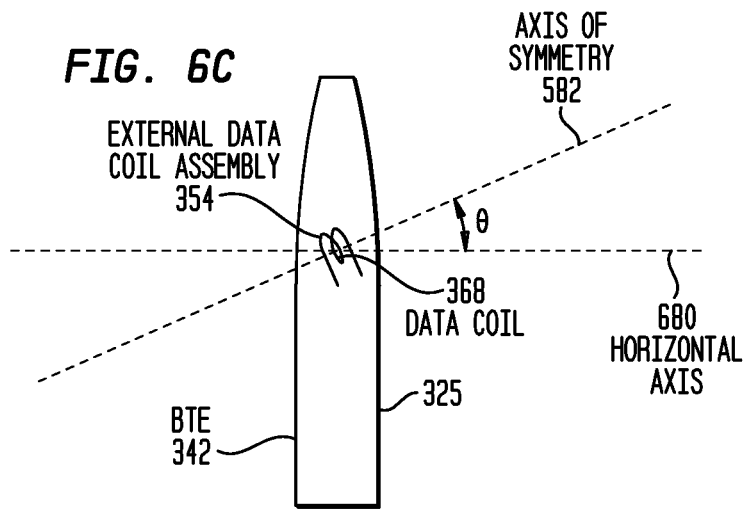

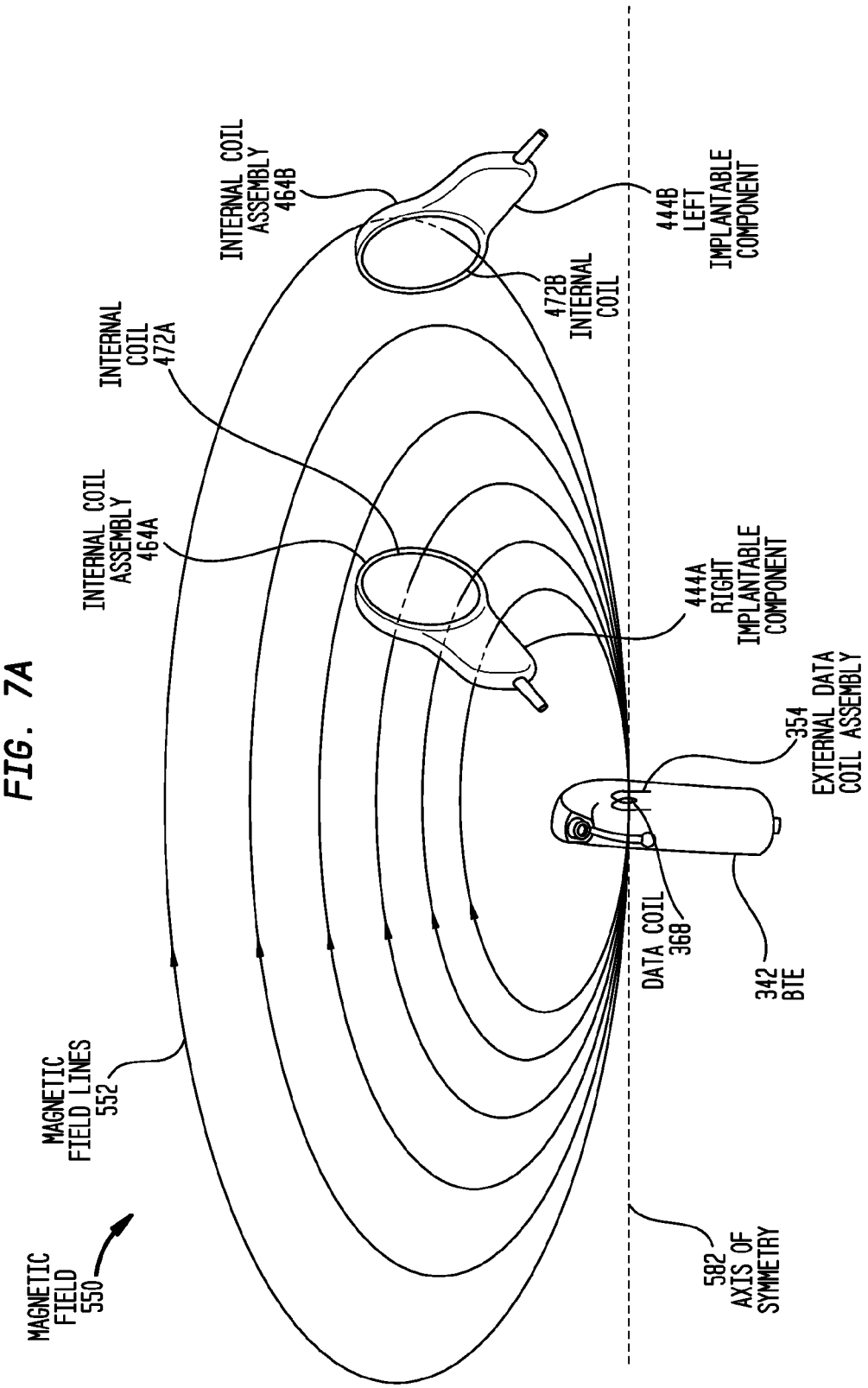

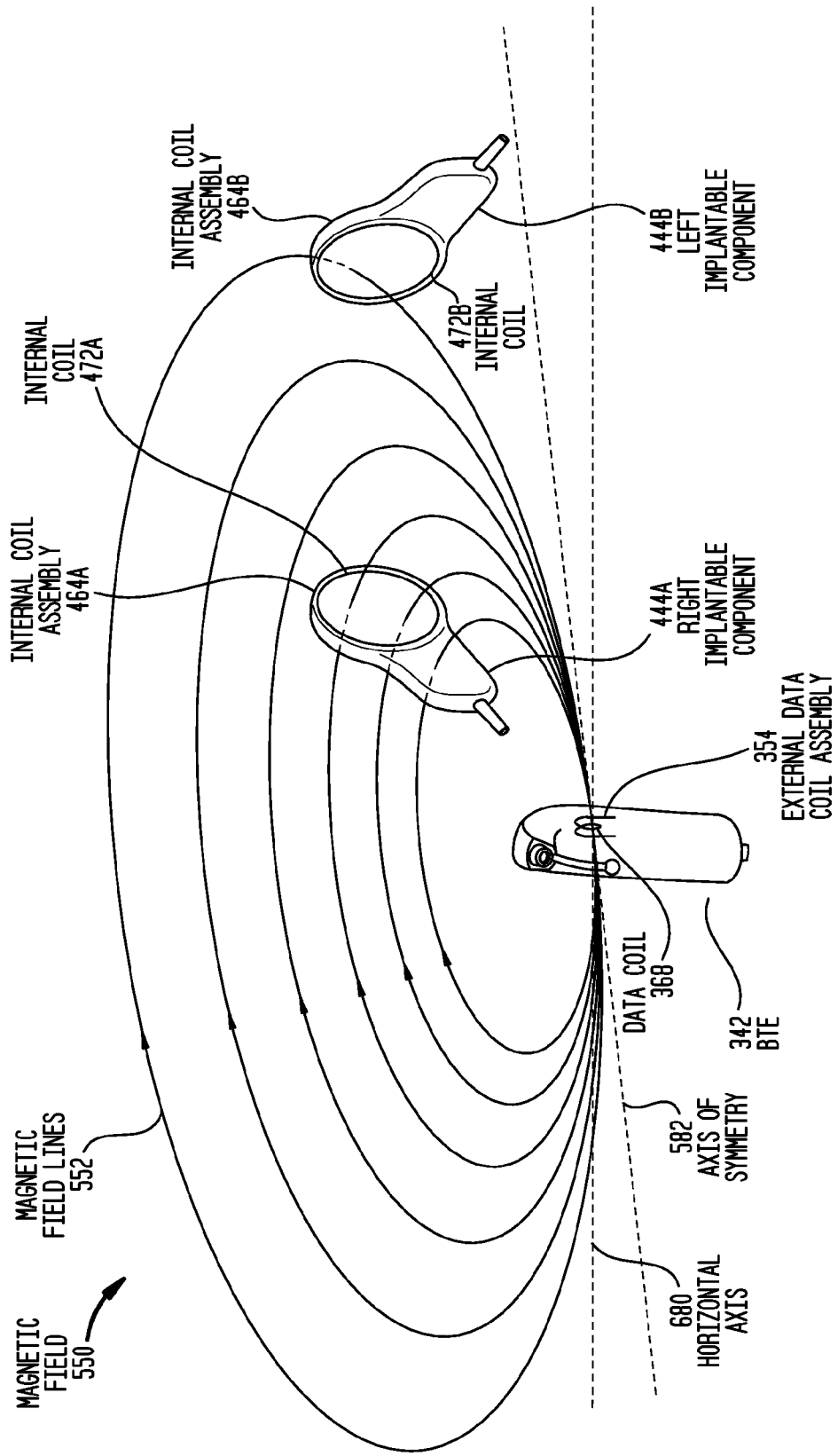

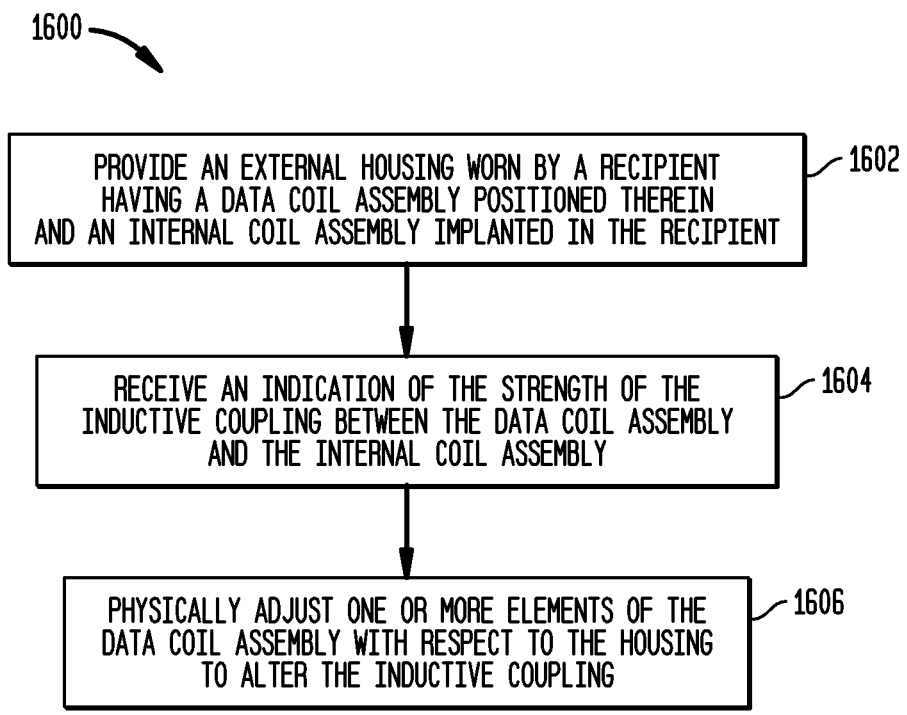

ADJUSTABLE TRANSCUTANEOUS ENERGY TRANSFER SYSTEM

CROSS-REFERENCE TO RELATED APPLICATIONS

This application is a National Stage Application of International Patent Application No. PCT/US09/39266, filed Apr. 2, 2009, which claims the benefit of Australian Provisional Application No. 2008901586; filed Apr. 2, 2008, both of which are hereby incorporated by reference herein.

BACKGROUND

1. Field of the Invention

The present invention relates generally to transcutaneous energy transfer in implantable medical devices and, more particularly, to an adjustable transcutaneous energy transfer system.

2. Related Art

Medical devices having one or more implantable components, generally referred to as implantable medical devices, have provided a wide range of therapeutic benefits to patients over recent decades. Implantable medical devices often include one or more instruments, apparatus, sensors, processors, controllers or other functional components that are permanently or temporarily implanted in a patient. The implanted components are used to, for example, diagnosis, monitor, or treat a disease or injury, or to modify the patient's anatomy or a physiological process. Many of these implantable components receive energy (i.e. power and/or data) from external components that are part of, or operate in conjunction with, the implantable component. Implantable hearing prostheses that treat the hearing loss of a prosthesis recipient are one particular type of implantable medical devices that are widely used today.

Hearing loss, which may be due to many different causes, is generally of two types, conductive and sensorineural. In some cases, a person suffers from hearing loss of both types. Conductive hearing loss occurs when the normal mechanical pathways for sound to reach the cochlea, and thus the sensory hair cells therein, are impeded, for example, by damage to the ossicles. Individuals who suffer from conductive hearing loss typically have some form of residual hearing because the hair cells in the cochlea are undamaged. As a result, individuals suffering from conductive hearing loss typically receive an implantable hearing prosthesis that generates mechanical motion of the cochlea fluid. Some such hearing prosthesis, such as acoustic hearing aids, middle ear implants, etc., include one or more components implanted in the recipient, and are referred to herein as implantable hearing prosthesis.

In many people who are profoundly deaf, however, the reason for their deafness is sensorineural hearing loss. Sensorineural hearing loss occurs when there is damage to the inner ear, or to the nerve pathways from the inner ear to the brain. As such, those suffering from some forms of sensorineural hearing loss are thus unable to derive suitable benefit from hearing prostheses that generate mechanical motion of the cochlea fluid. As a result, implantable hearing prostheses that deliver electrical stimulation to nerve cells of the recipient's auditory system have been developed to provide the sensations of hearing to persons whom do not derive adequate benefit from conventional hearing aids. Such electrically-stimulating hearing prostheses deliver electrical stimulation to nerve cells of the recipient's auditory system thereby providing the recipient with a hearing percept.

As used herein, the recipient's auditory system includes all sensory system components used to perceive a sound signal, such as hearing sensation receptors, neural pathways, including the auditory nerve and spiral ganglion, and parts of the brain used to sense sounds. Electrically-stimulating hearing prostheses include, for example, auditory brain stimulators and cochlear prostheses (commonly referred to as cochlear prosthetic devices, cochlear implants, cochlear devices, and the like; simply "cochlear implants" herein.)

Oftentimes sensorineural hearing loss is due to the absence or destruction of the cochlear hair cells which transduce acoustic signals into nerve impulses. It is for this purpose that cochlear implants have been developed. Cochlear implants provide a recipient with a hearing percept by delivering electrical stimulation signals directly to the auditory nerve cells, thereby bypassing absent or defective hair cells that normally transduce acoustic vibrations into neural activity. Such devices generally use an electrode array implanted in the cochlea so that the electrodes may differentially activate auditory neurons that normally encode differential pitches of sound. Auditory brain stimulators are used to treat a smaller number of recipients with bilateral degeneration of the auditory nerve. For such recipients, the auditory brain stimulator provides stimulation of the cochlear nucleus in the brainstem.

SUMMARY

In accordance with one aspect of the present invention, a hearing prosthesis is provided. The cochlear implant comprises: an internal coil assembly implantable in a recipient; and an external data coil assembly positioned in a housing worn by the recipient, wherein the data coil assembly is configured to be inductively coupled to the internal coil assembly in order to transcutaneously transfer data to the internal coil assembly, wherein one or more elements of the data coil assembly are physically adjustable with respect to the housing to alter the inductive coupling.

In accordance with another aspect of the present invention, a transcutaneous energy transfer system for an implantable medical device is provided. The system comprises: an internal coil assembly implantable in a recipient; and an external data coil assembly positioned in a housing worn by the recipient and configured to be inductively coupled to the internal coil assembly in order to transcutaneously transfer data to the internal coil assembly, wherein one or more elements of the data coil assembly are physically adjustable with respect to the housing to alter the inductive coupling.

In accordance with a still other aspect of the present invention, a method for using a hearing prosthesis comprising an internal coil assembly implantable in a recipient, and an external data coil assembly positioned in a housing worn by the recipient and configured to be inductively coupled to the internal coil assembly is provided. The method comprises: receiving an indication of the strength of the inductive coupling between the data coil assembly and the internal coil assembly; and physically adjusting one or more elements of the data coil assembly with respect to the housing to alter the inductive coupling between the data coil assembly and the internal coil assembly.

BRIEF DESCRIPTION OF THE DRAWINGS

Embodiments of the present invention are described below with reference to the attached drawings, in which:

FIG. 5 is a diagram illustrating the inductive coupling between an external component and an implantable component of a cochlear implant, in accordance with embodiments of the present invention;

FIG. 6A is a diagram illustrating the orientation of an external coil assembly in accordance with embodiments of the present invention;

FIG. 6B is a diagram illustrating the orientation of an external coil assembly in accordance with embodiments of the present invention;

FIG. 6C is a diagram illustrating the orientation of an external coil assembly in accordance with embodiments of the present invention;

FIG. 7A is a diagram illustrating the inductive coupling between an external component and two implantable components of a cochlear implant, in accordance with embodiments of the present invention;

FIG. 7B is a diagram illustrating the inductive coupling between an external component and two implantable components of a cochlear implant, in accordance with embodiments of the present invention;

FIG. 16 is a flowchart illustrating operations performed in accordance with embodiments of the present invention.

DETAILED DESCRIPTION

Figure 1:
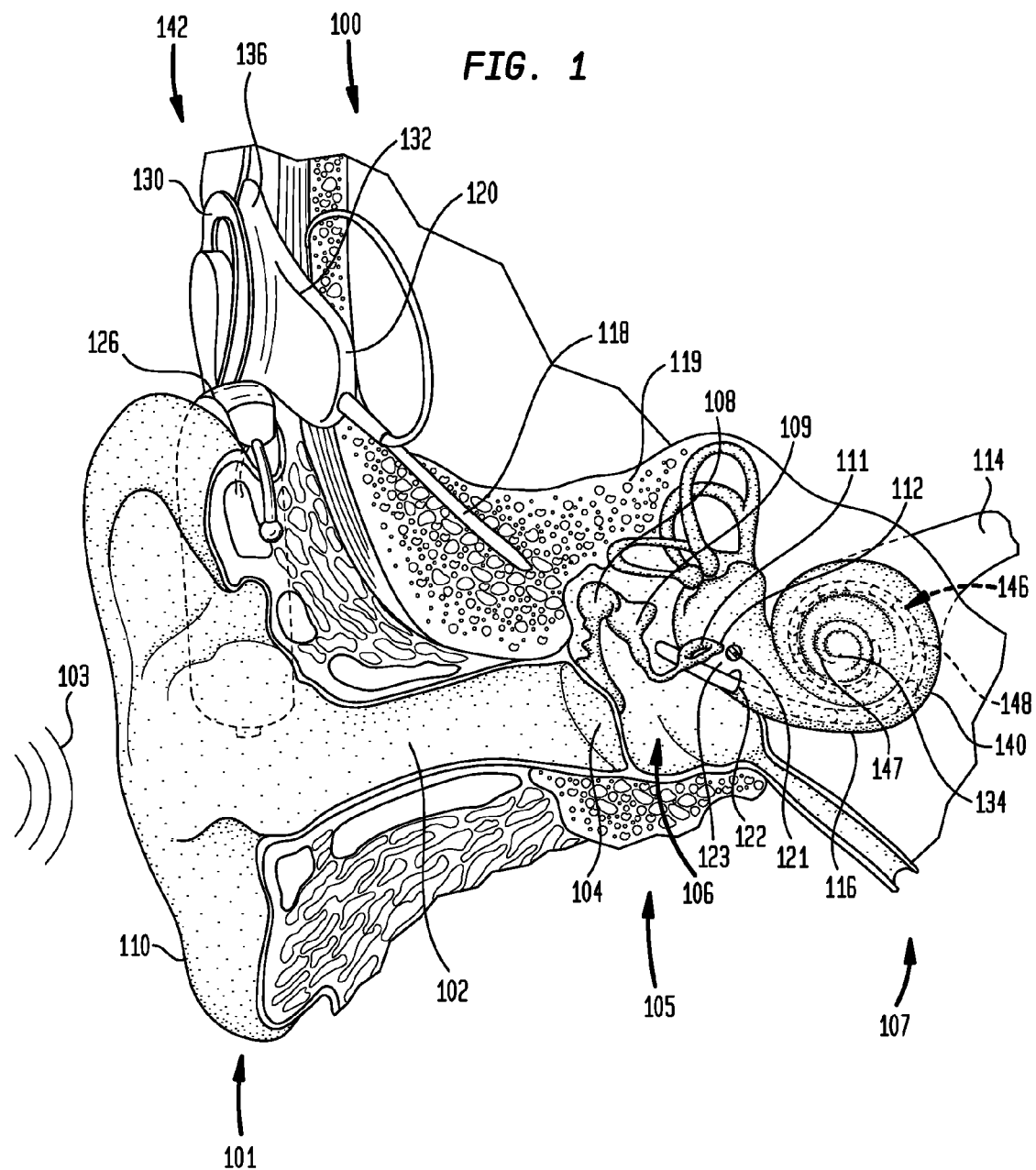
FIG. 1 is a perspective view of an exemplary medical device, namely a cochlear implant, in which embodiments of the present invention may be implemented.

Aspects of the present invention are generally directed to a transcutaneous energy transfer system for transferring data between components of an implantable medical device. The system comprises an internal coil assembly configured to be implanted in a recipient, and an external data coil assembly configured to be positioned in a housing worn on the recipient's head. The data coil assembly is further configured to be inductively coupled to the internal coil assembly. The inductive coupling is used to transcutaneously transfer data from the data coil assembly to the internal coil assembly. One or more elements of the data coil assembly are physically adjustable with respect to the housing to alter the inductive coupling between the data coil assembly and the internal coil assembly. Specifically, the external data coil assembly comprises a wire antenna coil having multiple turns of wire wound around a core. The position of at least one of the antenna coil and the core is physically adjustable with respect to the device housing to adjust the strength of the coupling between the data coil assembly and internal coil assembly.

As used therein, the transcutaneous transfer of energy refers to the transfer of data or power from an external device to an implanted device via a magnetic induction link. For example, transcutaneous energy transfer includes the inductive transfer of data over a weakly coupled magnetic induction link (by modulation of the H-field), or the transcutaneous transfer of power via a closely-coupled magnetic induction link operating in the reactive near field. The magnetic induction power and data links operate at radio frequencies (RF). Embodiments of the present invention will be primarily discussed herein with reference to the transcutaneous transfer of data via a magnetic induction link. However, it should be appreciated that embodiments of the present invention may be used for other types of transcutaneous energy transfer.

Although embodiments of the present invention are described herein primarily in connection with one type of implantable medical device, namely a cochlear prosthesis (commonly referred to as a cochlear prosthetic device, cochlear implant, cochlear device, and the like; simply "cochlear implants" herein), it would be appreciated that embodiments of the present invention may be implemented in any implantable medical device now known or later developed. Implantable medical devices envisaged by the present invention include, but are not limited to, cardiac monitors and defibrillators; glucose meters; implantable drug pumps; neural stimulators, including vision and hearing prostheses such auditory brain stimulators, or other devices that electrically, acoustically or mechanically stimulate components of the recipient's outer, middle or inner ear. It would also be understood that the present invention, though particularly applicable to implantable medical devices, may also be applied to a wide variety of other medical devices that do not include an implantable device.

FIG. 1 is perspective view of a cochlear implant in accordance with embodiments of the present invention, referred to as cochlear implant 100, implanted in a recipient. The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

In the embodiments of FIG. 1, cochlear implant 100 comprises an external component 142 which is directly or indirectly attached to the body of the recipient, and an internal or implantable component 144 which is temporarily or permanently implanted in the recipient. As shown, external component 142 comprises a housing 126 that is configured to be worn behind the ear of the recipient, referred to as Behind-The-Ear (BTE) unit 126. Disposed in or on BTE 126 are one or more sound input elements, shown as microphone 124 for detecting sound 103. It would be appreciated that a sound input element in accordance with embodiments of the present invention may comprise a microphone or an electrical input which connects cochlear implant 100 to, for example, FM hearing systems, MP3 players, televisions, mobile phones, etc.

As discussed in detail below, BTE 126 includes a data transceiver unit (not shown) to transmit data to implantable component 144. In certain embodiments, the data transceiver unit is configured to inductively transmit electrical signals representing the output of microphone 124 to implantable component 144. BTE 126 may also comprise one or more other functional components to generate data which is provided to implantable component 144 via the data transceiver unit. In some embodiments, the data transceiver unit is configured to inductively receive data from implantable component 144.

External component 142 further comprises a power transmitter unit 131 which provides power from an external power source (not shown) to implantable component 144. The power source may be disposed in BTE 126, or may comprise a separate component. As shown, power transmitter unit 131 comprises an external power coil 130, and, preferably, a magnet (not shown) secured directly or indirectly to external coil 130. Power coil 130 is typically a wire antenna coil comprised of multiple turns of electrically insulated single-strand or multi-strand conducting wire, such as, for example, platinum or gold wire. Power transmitter unit 131 further includes a power transmitter (also not shown) which operates with external coil 130 to transmit power to internal component 144.

In certain embodiments of the present invention, external component 142 comprises a single device that includes power transmitter unit 131 and BTE 126. In such embodiments, one or more elements of power transmitter unit 131 may be disposed in BTE 126 and the BTE would be connected to coil 130 via a cable. It would be appreciated that in alternative embodiments of the present invention, power transmitter unit 131 and BTE 126 comprise separate devices that operate independently of one another.

As described in detail below, implantable component 144 comprises a transceiver unit 132 which may be positioned in a recess of the temporal bone adjacent auricle 110 of the recipient. As detailed below, transceiver unit 132 is inductively coupled to the data transceiver unit in BTE 126 and to power transmitter unit 131. That is, transceiver unit 132 wirelessly receives data and power from the data transceiver unit and from power transmitter unit 131, respectively, via radio frequency (RF) links. Transceiver unit 132 comprises an internal coil 136, and preferably, a magnet (also not shown) fixed relative to the internal coil. Internal coil 136 is typically a wire antenna coil comprised of multiple turns of electrically insulated single-strand or multi-strand conducting wire, such as, for example, platinum or gold wire.

Implantable component 144 further comprises a stimulator unit 120 and an elongate electrode assembly 118. Internal receiver unit 132 and stimulator unit 120 are hermetically sealed within a biocompatible housing, sometimes referred to herein as main implantable component 120. Elongate electrode assembly 118 has a proximal end connected to main implantable component 120, and a distal end implanted in cochlea 140. Electrode assembly 118 extends from main implantable component 120 to cochlea 140 through mastoid bone 119. Electrode assembly 118 is inserted or implanted into cochlea 140. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, sometimes referred to as electrode array 146 herein, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals which are applied by electrodes 148 to cochlea 140, thereby stimulating auditory nerve 114.

As noted, FIG. 1 illustrates specific embodiments of the present invention in which cochlear implant 100 includes an external component 142. It would be appreciated that in alternative embodiments, cochlear implant 100 comprises a totally implantable prosthesis that is capable of operating, at least for a period of time, without the need of an external component. In such embodiments, all components of cochlear implant 100 are implantable, and the cochlear implant operates in conjunction with external component 142.

Figure 2:
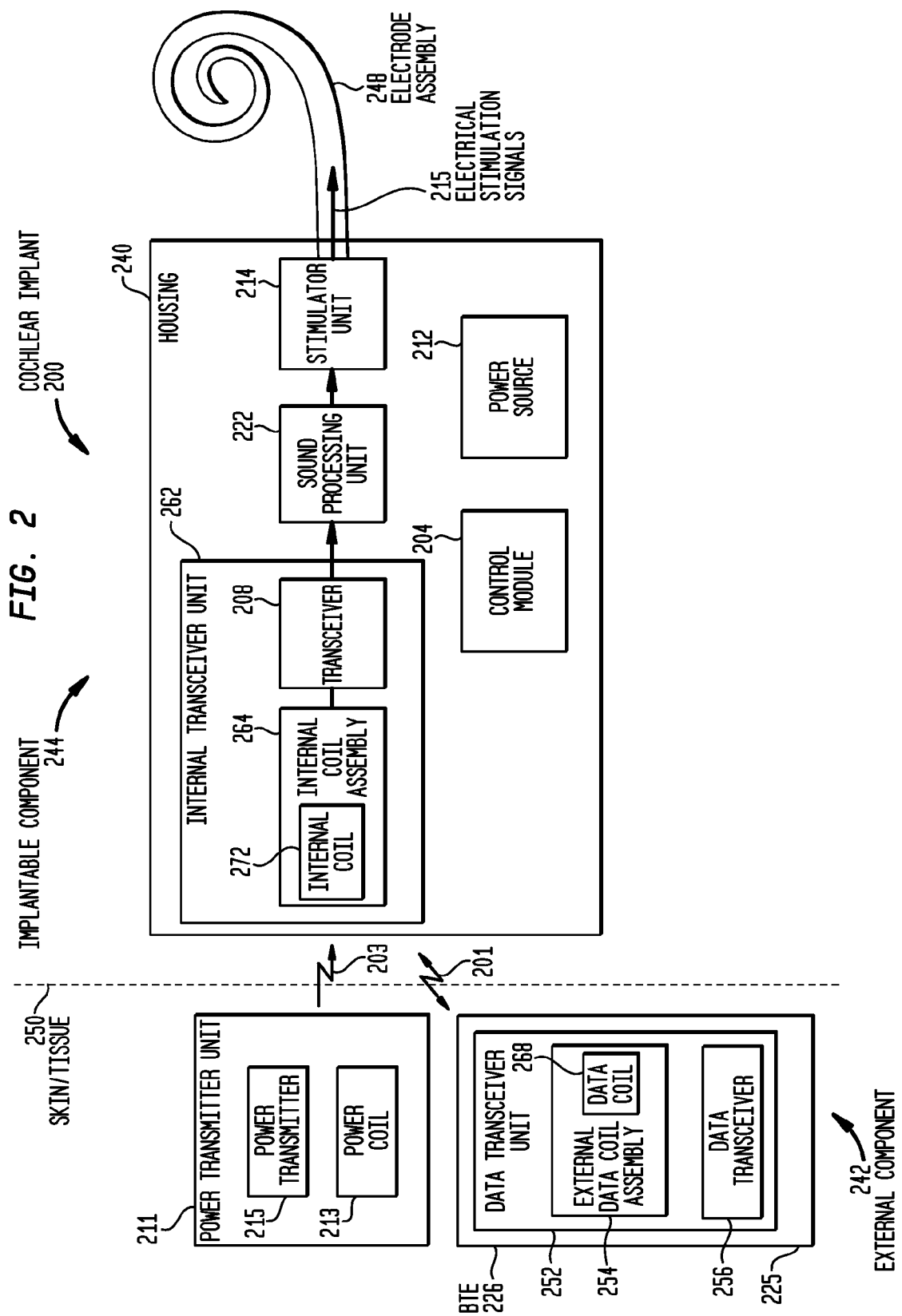
FIG. 2 is a functional block diagram of a cochlear implant, in accordance with embodiments of the present invention.

FIG. 2 is a functional block diagram of embodiments of cochlear implant 100 in which embodiments of the present invention may be implemented, referred to as cochlear implant 200 herein. Similar to the above embodiments, cochlear implant 200 comprises an external component 242 and an implantable component 244 configured to be implanted under skin/tissue 250 of a recipient.

External component 242 comprises BTE 226 having a housing 225 and a data transceiver unit 252 positioned in the housing. Data transceiver unit 252 includes an external data coil assembly 254 comprising a wire antenna coil, referred to as external data coil 268. Data transceiver unit 252 further includes data transceiver 256 comprising electrical circuit components utilized with data coil 268 to inductively transmit data 201 to, or receive data from, internal transceiver unit 262 in implantable component 244. In certain embodiments, data transceiver unit 252 is configured to receive data from implantable component 244. That is, the transfer of data 201 between internal transceiver unit 262 and data transceiver unit 252 may be bi-directional, shown by bi-directional arrow 201.

Embodiments of the present invention will be primarily discussed herein with reference to components capable of bi-directional data transfer. However, it should be appreciated that the embodiments described herein are merely illustrative and do not limit the scope of the present invention. For example, in other embodiments, the data transceiver unit 252 is configured as a data transmitter unit which transmits, but does not receive data. Similarly, internal transceiver unit 262 may be configured as a data receiver unit which receives, but does not transmit data.

In certain configurations, external component may further comprise a power transmitter unit 211. Power transmitter unit 211 is provided when it is desirable to transcutaneously transfer power to implantable component 244. Power transmitter unit 211 includes a wire antenna coil, referred to as external power coil 213, and power transmitter 215 connected to a power source (not shown). Power transmitter 215 comprises electrical circuit components utilized with power coil 213 to inductively transmit power 203 to internal transceiver unit 262 in implantable component 244.

In embodiments of the present invention, power transmitter unit 211 and data transceiver unit 268 comprise separate components that may be used independently. For example, in certain embodiments, power transmitter unit 211 is only provided or utilized when it is desirable to transmit power to implantable component 244.

As noted, implantable component 244 comprises an internal transceiver unit 262 which inductively receives data 201 or power 203 from data transceiver unit 252 and power transmitter unit 211, respectively. Thus, internal transceiver unit 262 refers to a collection of one or more implanted components which form part of a transcutaneous energy transfer link with data transceiver unit 252 or power transmitter unit 211. More specifically, internal transceiver unit 262 comprises an internal coil assembly 264 having an internal coil 272 configured to form magnetic induction links with power coil 213 or data coil 268. Transceiver 208 comprises electrical circuit components configured to decode the electrical output of internal coil 272 and to distribute the received power and data. Transceiver 208 is electrically connected to internal coil 272 via one or more electrical leads 209. Details of the inductive transfer of power and data are provided below.

Cochlear implant 200 further comprises a sound processing unit 222, stimulator unit 214 and control module 204. In the embodiments of FIG. 2, data 201 received by internal transceiver unit 262 is provided to sound processing unit 222. Sound processing unit 22 implements one or more speech processing and/or coding strategies to convert data 201 into data signals 210 which are provided to stimulator unit 214. Based on data signals 210, stimulator unit 214 generates electrical stimulation signals 215 for delivery to the cochlea of the recipient. In the embodiment illustrated in FIG. 2, cochlear implant 200 comprises an embodiment of electrode assembly 118 of FIG. 1, referred to as electrode assembly 248, for delivering stimulation signal 215 to the cochlea.

Cochlear implant 200 also includes rechargeable power source 212. Power source 212 may comprise, for example, one or more rechargeable batteries. As noted above, power 203 is received from power transmitter unit 211, and is distributed immediately to desired components, and/or is stored in power source 212. In the embodiments of FIG. 2, power may be distributed from power source 212 to the other components of cochlear implant 200 as needed for operation. For ease of illustration, electrical connections between power source 212 and the other components of implantable component 244 have been omitted.

Implantable component 244 further comprises control module 204. Control 204 includes various components for controlling the operation of cochlear implant 200, or for controlling specific components of cochlear implant 200. For example, control module 204 may control the delivery of power from power source 212 to other components of cochlear implant 200. For ease of illustration, electrical connections between control module 204 and the other components of implantable component 244 have been omitted.

In the embodiments of FIG. 2, internal transceiver unit 262 is shown integrated in a biocompatible housing 240 with sound processing unit 222, stimulator unit 214, control module 204 and power source 212. It would be appreciated that one or more of the illustrated elements may be disposed in a separate housing.

Furthermore, the present invention is primarily further described herein with reference to the transfer of data from an external component to an implantable component. It would be appreciated that this transfer is merely illustrative, and the other types of transfer, such as bi-directional data transfer, are within the scope of the present invention.

Figure 3A:
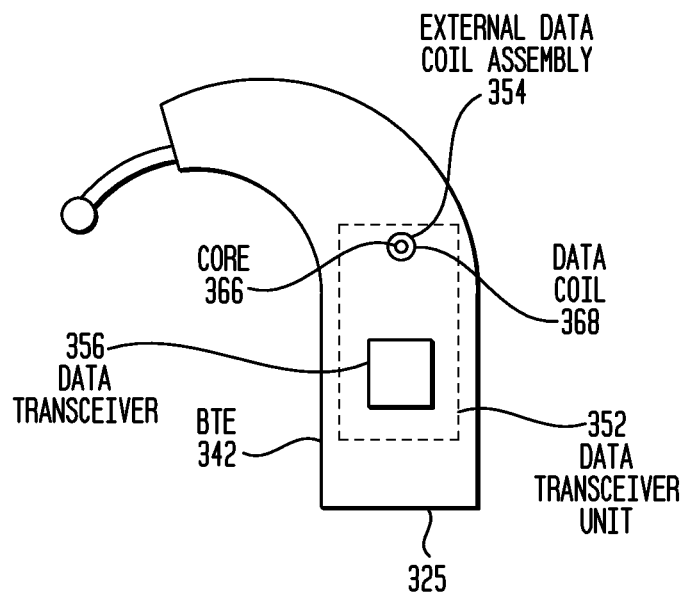
FIG. 3A is cross-sectional side view of an external component of a cochlear implant, in accordance with embodiments of the present invention.
Figure 3B:
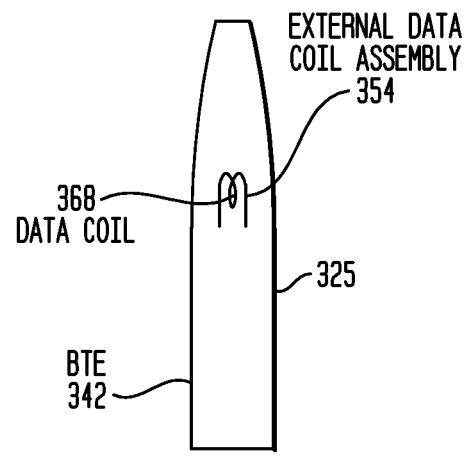
FIG. 3B is cross-sectional front view of an external component of a cochlear implant, in accordance with embodiments of the present invention.

As noted above, a cochlear implant in accordance with embodiments of the present invention includes an external component configured to transcutaneously transmit data to one or more implanted components of the cochlear implant. FIGS. 3A and 3B illustrate one exemplary arrangement of an external data transmitting component, referred to as Behind-The-Ear (BTE) unit 342. Embodiments of the present invention will be primarily discussed herein with reference to BTE 342, but it would be appreciated that other arrangements of an external data transmitting component are within the scope of the present invention.

FIG. 3A is a schematic side-view of BTE 342 in accordance with embodiments of the present invention. As shown, BTE 342 comprises a collection of one or more components, referred to as data transceiver unit 352, which form part of a transcutaneous energy transfer link with a transceiver unit in an implanted portion of the cochlear implant. More specifically, data transceiver unit 352 comprises an external data coil assembly 354 configured to transmit data to, or receive data from, the implanted portion of the cochlear implant. External data coil assembly 354 comprises a data coil 368 wound around core 366 and is a positioned in housing 325 worn on the recipient's head. Similar to the embodiments described above, data coil 368 is a wire antenna coil comprised of multiple turns of electrically insulated single-strand or multi-strand conducting wire, such as, for example, platinum or gold wire. As detailed below, core 366 is positioned between, and circumferentially surrounded by, the turns of data coil 368. Core 366 may comprise, for example, air or a material having a higher permeability, such as a ferromagnetic material. Data coil 368 is configured to form a magnetic induction link with an implanted coil.

As detailed below, the position of at least one of data coil 368 and core 366 is physically adjustable with respect to BTE housing 325 to alter the magnetic coupling between data coil assembly 354 and an implanted data coil. That is, the orientation, position, arrangement, etc., of one or more of external data coil 368 or the core is physically adjustable to alter the inductive coupling. As described below, the coil or core of external data coil assembly 354 may be adjusted in a variety of manners, and the various adjustments may have different affects on the inductive coupling.

Data transceiver unit 352 further comprises electrical circuit components which operate with data coil 368 to transmit or receive the data, referred to as data transceiver 356. Data transceiver 356 is electrically connected to data coil 368 via one or more electrical leads (not shown) and provides electrical signals to data coil 368 resulting in the transmission of data to the internal transceiver unit of the cochlear implant.

FIG. 3B is schematic view of BTE 342 of FIG. 3A. For ease of illustration, only external data coil assembly 354, and specifically only coil 368, is shown. FIGS. 5-9 illustrate embodiments of the present invention with reference to the schematic view of BTE 342 shown in FIG. 3B.

Figure 4A:
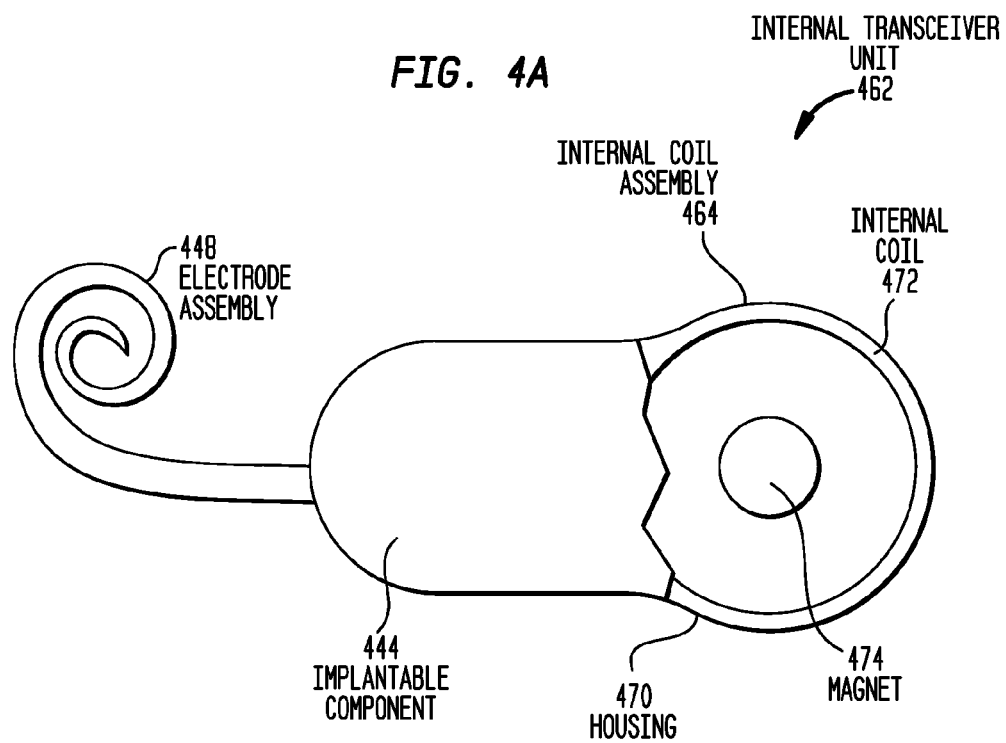
FIG. 4A is partial cross-sectional perspective view of an implantable component of a cochlear implant, in accordance with embodiments of the present invention.
Figure 4B:
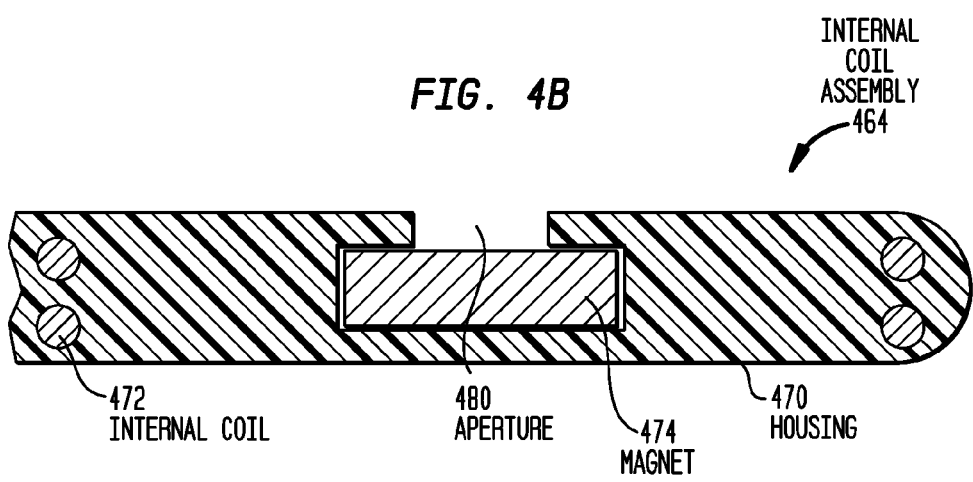
FIG. 4B is cross-sectional side view of an implantable component of a cochlear implant, in accordance with embodiments of the present invention.

As noted above, a cochlear implant in accordance with embodiments of the present invention further includes an implantable component configured to transcutaneously receive data from an external data transmitting component, such as BTE 342 of FIGS. 3A and 3B. FIGS. 4A and 4B illustrate one exemplary arrangement of an implantable component 444. Embodiments of the present invention will be primarily discussed herein with reference to implantable component 444, but it would be appreciated that other arrangements of an implantable component are within the scope of the present invention. Furthermore, for ease of illustration, the embodiments of FIGS. 4A and 4B will be discussed with reference to BTE 342 and the components thereof.

FIG. 4A is a perspective, partial cross-sectional side-view of implantable component 444. As shown, implantable component comprises a collection of one or more components, referred to as internal transceiver unit 462, which form part of a transcutaneous energy transfer link with data transceiver unit 352. More specifically, internal transceiver unit 462 comprises an internal coil assembly 464. Internal coil assembly 464 comprises a wire antenna coil 472 comprised of multiple turns of electrically insulated single-strand or multi-strand wire configured to form a magnetic induction link with external data coil 268. In certain embodiments, internal coil assembly 464 may comprise a core positioned between, and circumferentially surrounded by, the turns of coil 472. In such embodiments, the core may comprise, for example, air, a ferromagnetic material, etc.

Embodiments of the present invention will be primarily discussed herein with reference to a single internal coil 472. It should be appreciated that in certain embodiments, two internal coils may be provided. In such embodiments, a first internal coil may be used to transmit/receive data while the second internal coil is used to receive power.

Internal transceiver unit 462 further comprises electrical circuit components, referred to as a transceiver (not shown), configured to decode the electrical output of internal coil 472 and to distribute the received data to desired elements of implantable component 444. Disposed in internal coil assembly 464 is a magnet 474. As noted above with reference to FIG. 1, magnet 474 may be used to couple a power transmitter unit (FIG. 1) or a power coil (FIG. 1) to the recipient.

In the embodiments of FIGS. 4A and 4B, internal transceiver unit 462 is integrated in a biocompatible housing 470 with one or more other functional components of implantable component 444. For example, in certain embodiments, a sound processing unit, stimulator unit, a control module and a power source (all not shown) are integrated in housing 470 with internal transceiver unit 462. It would be appreciated that one or more of the above elements may be disposed in a separate housing. Extending from housing is an embodiment of electrode assembly 118 of FIG. 1, referred to as electrode assembly 448.

FIG. 4B is cross-sectional side view of internal coil assembly 464 of FIG. 4A. As noted above, internal coil assembly 464 is disposed in a biocompatible housing 470. Specifically, internal coil 472 is embedded in housing 470. In embodiments of the present invention, biocompatible housing 470 may comprise any suitable flexible material, such as silicone or other polymer.

Also shown in FIG. 4B, housing 470 has an aperture 480 through which magnet 474 may be inserted. As noted, housing 470 may comprise a flexible material, thus the orientation of one or more portions of housing 470 near aperture 480 may be manipulated to enable insertion of magnet 474. Once positioned in housing 470, magnet 474 is substantially surrounded by housing 470, and is retain in position by the housing.

As noted above, FIGS. 5-9 illustrate embodiments of the present invention with reference to the schematic view of BTE 342 shown in FIG. 3B. FIGS. 5-9 further illustrate the embodiments of the present invention with reference to a schematic view of implantable component 444. Furthermore, FIGS. 5-9 describe embodiments of the present invention with reference to the implantation of implantable component 444 in a recipient's head, and with the positioning of BTE 342 on a recipient's ear. For ease of illustration, the recipient's head and ear are not shown in FIGS. 5-9.

FIG. 5 is a diagram illustrating the inductive transfer of data from external data coil assembly 354 of BTE 342 to internal coil assembly 464 of implantable component 444 in accordance with embodiments of the present invention. As is well known, the inductive transfer of data refers to the transfer of energy from one element, such as a coil antenna, to another coil antenna through an inductive coupling between the antennas. Inductive coupling, sometimes referred to as magnetic coupling, between two coil antennas occurs when a varying magnetic field exists between the antennas. That is, coil antennas are inductively coupled when a change in current flow through one antenna, referred to as the transmitting antenna, induces a voltage across the ends of the other antenna, referred to as receiving antenna, via an magnetic field generated by the transmitting coil antenna.

In the embodiments of FIG. 5, external data coil assembly 354 functions as a transmitting antenna. As noted, data coil 368 is a wire antenna coil comprised of multiple turns of electrically insulated single-strand or multi-strand wire. A current through the turns of data coil 368 will generate a magnetic field 555 having exemplary magnetic field lines 552. The time-varying magnetic flux associated with magnetic field 555 results in a voltage over internal coil 472.

As is well known, a generated magnetic field is substantially symmetrical about a longitudinal axis extending approximately through the geometric center of the area bounded by the turns of the transmitting coil. This axis is referred to herein as axis of symmetry 582. Thus, as used herein, axis of symmetry 582 refers to a longitudinal axis through the center of data coil 368, as well as the symmetrical axis of magnetic field 550. For ease of illustration, only the half of magnetic field 550 which is in the direction of implantable component 444 is shown.

Also as known, a magnetic field such as field 550 attenuates as the distance from data coil 368 increases. Furthermore, magnetic field lines 552 follow a certain pattern depending on, for example, the orientation, position, geometry, arrangement, etc., generally and collectively referred to as the configuration of, external data coil assembly 354. Thus, only a fraction of the magnetic flux generated by external data coil assembly 354, represented by field lines 552, will reach internal coil 472. The more magnetic flux that reaches internal coil 472, the better or stronger data coil 368 and internal coil 472 are coupled. The coupling strength between coils 368, 372 may be expressed by a coupling factor k. The coupling factor is a value between zero and one. A coupling factor of 1 indicates a perfect coupling between coils 368, 372 (i.e. all flux generated by external data coil assembly 354 is received by internal coil 472), while a coupling factor of zero indicates that coils 368, 372 are independent (i.e. no magnet flux generated by external data coil assembly 354 is received by internal coil 372).

In the illustrative embodiments of FIG. 5, external data coil assembly 354 is configured such that there is a strong inductive coupling between data coil 368 and internal coil 472. That is, a significant portion of magnetic flux generated by external data coil assembly 354 is received by internal coil 472, resulting in a large coupling coefficient.

The external coil and internal coils of conventional cochlear implants and other implantable medical devices typically each have a fixed configuration. In other words, the orientation, position, arrangement, etc. of conventional transmitting and receiving coils in a medical device used to inductively transmit data are fixed during manufacture, and are not adjustable at a later time. However, the fixed coil configurations may make it difficult for a surgeon to obtain a strong inductive coupling between transmitting and data coils of the implantable medical device. For example, most implantable medical devices are designed to be implanted in a variety of recipients, and are typically not designed and/or constructed to be implanted in a specific recipient. As such, due to, for example, different patient head sizes, skull shapes, skin/tissue thickness, ear location, surgeon preference of implant location, etc., the use of fixed coil configurations in a generic device may provide a sufficiently strong inductive coupling only in certain recipients, and may make it difficult to obtain the desired coupling between the transmitting/receiving coils in other recipients. Furthermore, in such devices, slight movements/vibrations of the BTE due to the loose attachment of the BTE to the recipient's ear could cause undesirable changes in the inductive coupling between fixed coil configurations.

Embodiments of the present invention avoid the above and other drawbacks by providing the ability to alter the inductive coupling between data coil 368 and implanted internal coil 472. In embodiments of the present invention, the configuration of external data coil assembly 354 is physically adjustable in order to alter the inductive coupling between coils 368, 372. Specifically, the orientation or physical position of at least one of data coil 368 and core 366 is physically adjustable with respect to housing 325 to alter the coupling between coils 368, 372.

As described in detail below, in accordance with embodiments of the present invention, data coil 368 and the core of external data coil assembly 354 may be adjusted in a variety of manners to alter the magnetic coupling between coils 368, 372. Also as described below, the physical adjustment of the elements may have different affects on the magnetic field that is generated by the external data coil assembly.

For example, in certain embodiments of the present invention, the coupling between coils 368 and 372 is altered by changing the orientation or position of axis of symmetry 582 of magnetic field 550. In other embodiments, the coupling between coils 368 and 372 is altered by changing the flow of magnetic flux within magnetic field 550. The flow of magnetic flux within magnetic field 550 is visualized by magnetic field lines 552. Thus, changing the flow of magnetic flux within magnetic field 550 may be viewed as a change in the location of magnetic field lines 552 within the field. The above and other methods for altering the inductive coupling are described below.

FIGS. 6A-6C illustrate embodiments of the present invention in which the inductive coupling between data coil 368 and internal coil 472 may be altered through adjustment of the orientation of axis of symmetry 582. FIG. 6A illustrates an exemplary starting position of external data coil assembly 354 within housing 325 of BTE 342. Specifically, BTE 342 and external data coil 368 are positioned substantially vertically with each of the wires coils of the data coil being substantially parallel to a recipient's head. Thus, axis of symmetry 582 is substantially co-axial with a horizontal axis (not shown) that extends through the recipient's skull. For ease of illustration, magnet field lines 552 have been omitted from FIGS. 6A-6C. However, it would be appreciated that magnetic field lines 552 would be substantially symmetrical about axis of symmetry 582.

As noted above, the starting position of data coil 368 may not provide a desired inductive coupling for all recipients between the data coil and implanted internal coil 372. FIGS. 6B and 6C illustrate adjustments of the orientation of axis of symmetry 582 in order to alter the coupling between coils 368, 372. Specifically, in the embodiments of FIGS. 6B and 6C, one or more elements of external data coil assembly 354 are physically adjusted to shift the orientation of axis of symmetry 582 by an angle theta ($\theta$) from horizontal axis 680. As would be appreciated, axis of symmetry 582 may be shifted by any number of angles $\theta$, and the shift may be vertical shifts (as shown in FIGS. 6B and 6C), or may be horizontal or lateral shifts from horizontal axis 680. Vertical shifts refer to shifts in which axis of symmetry 582 remains in the same vertical plane as horizontal axis 680. Horizontal or lateral shifts refer to shifts in which axis of symmetry 582 remains in the same horizontal plane as horizontal axis 680. As would be appreciated, in certain embodiments, combinations of vertical and lateral shifts may be provided to adjust the orientation of axis of symmetry 582. In such embodiments, axis of symmetry 582 would be shifted a horizontal angle $\theta$, and by a vertical angle $\theta$.

As noted, one or more elements of external data coil assembly 354 are adjusted in order to provide the change in orientation of axis of symmetry 582 described above. As shown in FIGS. 6A and 6B, a physical change in the orientation of data coil 368 with respect to housing 325 and the recipient's head provides a corresponding change in the orientation of axis of symmetry 582. As noted, axis of symmetry refers to a longitudinal axis extending approximately through the geometric center of the area bounded by the turns of data coil 368. Thus, a change in the orientation of coils 368 with respect to housing 325 by an angle $\theta$ results in a corresponding change in the orientation of axis of symmetry by an angle $\theta$. The physical adjustment of the one or more elements of external data coil assembly 368 to provide the desired change in orientation is described below with reference to FIGS. 13 and 14.

FIGS. 7A and 7B are schematic diagrams illustrating the inductive coupling between an external data assembly 354 of BTE 342 and internal coils 472 of two implantable components 444 of a cochlear implant. In these embodiments, the cochlear implant comprises a bilateral system having a first implantable component 444A positioned near the right side of the recipient's skull, referred to as right implantable component 444A. The cochlear implant further comprises a second implantable component 444B positioned near the left side of the recipient's skull, referred to as left implantable component 444B. BTE 342 is positioned adjacent the recipient's right ear. Also as shown, data coil 368 is positioned such that axis of symmetry 582 is substantially co-axial with a horizontal axis (not shown) extending through the recipient's skull. For ease of illustration, the recipient's ear and skull are not shown.

In the embodiments of the present invention shown in FIG. 7A, data coil 368 is strongly coupled to internal coil 472A of right implantable component 444A. That is, a significant amount of magnetic flux generated by external data coil assembly 354 is received by internal coil 472A so as to enable inductive data transmission between data coil 368 and internal coil 472A. However, in FIG. 7A, data coil 368 is weakly coupled to internal coil 472B of left implantable component 444A. That is, a low amount of magnetic flux generated by external data coil assembly 354 is received by internal coil 472B, thus preventing inductive data transmission between data coil 368 and internal coil 472B. As described below, one or more components of external data coil assembly 354 are adjustable to alter the inductive coupling between data coil 368 and coils 472.

FIG. 7B illustrates the cochlear implant of FIG. 7A in which data coil 368 is sufficiently coupled to both internal coils 472A and 472B so as to enable inductive data transmission between all coils. Specifically, in the embodiments of FIG. 7B, one or more elements of external data coil assembly 354 are physically adjusted from the configuration shown in FIG. 7A to change the orientation of data coil 368 with respect to the recipient's head, and thus axis of symmetry 582. This change in orientation may be substantially similar to the changes discussed above with reference to FIGS. 6B and 6C. The physical adjustment of one or more elements of data coil assembly 354 to change the orientation of data coil 368 and thus axis of symmetry 582 is described below with reference to FIGS. 13 and 14.

The change in the orientation of axis of symmetry 582 also changes the flow of magnetic flux within magnetic field 550, shown by the change in location of magnetic field lines 552 of FIG. 7B. Thus, as shown, the change in orientation of axis of symmetry 582 causes additional magnetic flux to be received by internal coil assembly 464B. The additional magnetic flux provides a desired inductive coupling between data coil 368 and internal coil 472B that is sufficient to enable data transmission between coils 368 and 472B.

As would be appreciated, the change in the orientation of axis of symmetry 582 from horizontal axis 680 will also alter the amount of magnetic flux received by internal coil 472A. Thus, in embodiments of the present invention, the orientation of data coil 368 is changed to ensure that sufficient magnetic flux is received by both internal coils 472. In such embodiments, the inductive coupling between data coil and each of internal coils 472 may not be as strong as in alternative configurations, but is sufficiently strong to enable the desired data transmission.

Figure 8:
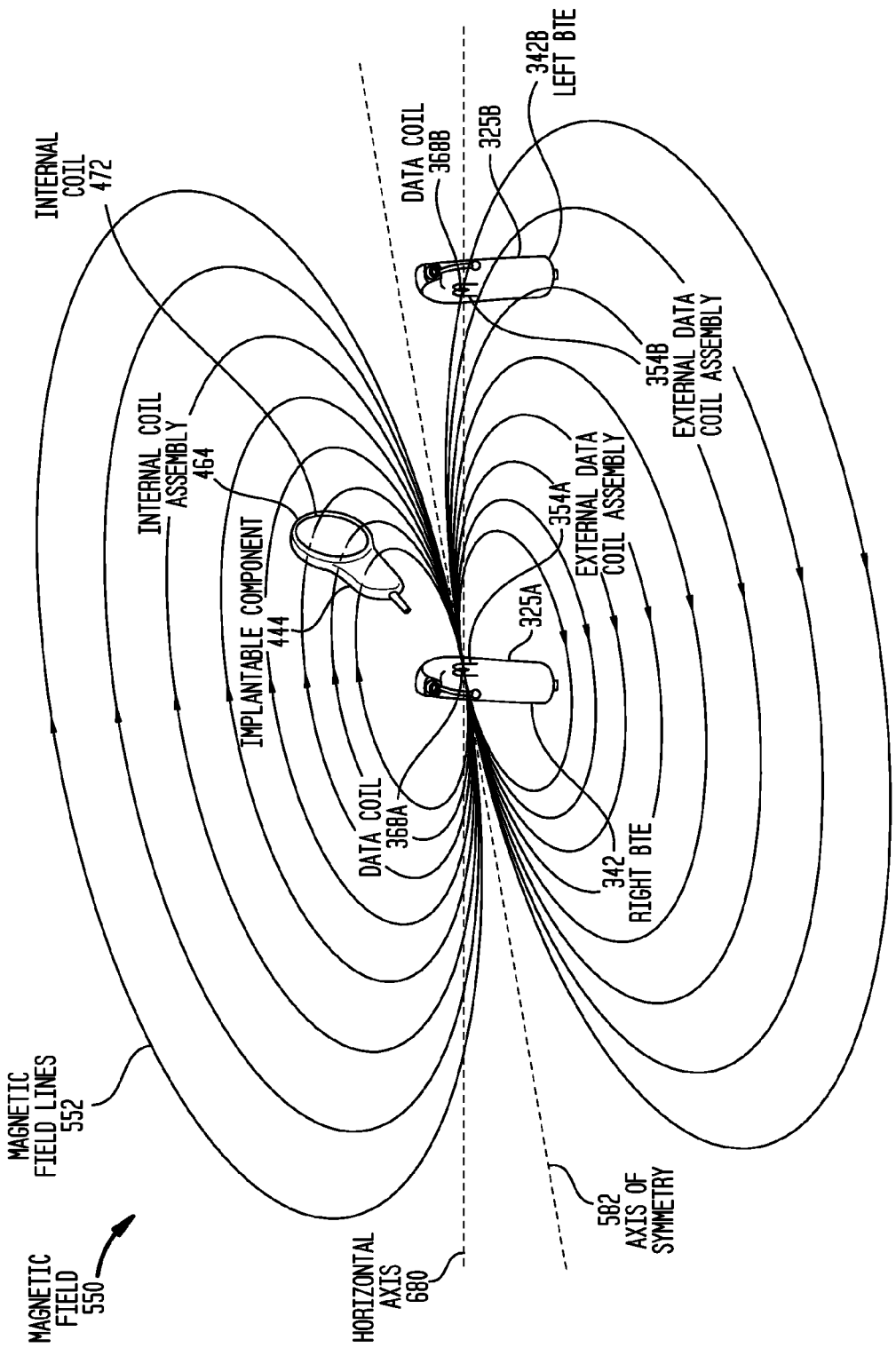
FIG. 8 is a diagram illustrating the inductive coupling between two external components and an implantable component of a cochlear implant, in accordance with embodiments of the present invention.

FIG. 8 is a schematic diagram of a cochlear implant illustrating the inductive coupling between an external data coil assembly 354A of a first BTE 342A, an internal coil assembly 462 of an implantable component 444, and an external coil assembly 354B of a second BTE 342B. In these embodiments, the cochlear implant comprises a bilateral system having first BTE 342A positioned adjacent the recipient's right ear, referred to as right BTE 342A. The second BTE 342B is positioned adjacent the recipient's left ear and is referred to as left BTE 342B. The cochlear implant further comprises an implantable component 444A positioned near the right side of the recipient's skull.

In the embodiments of the present invention shown in FIG. 8, data coil 368A is configured to inductively transmit data to internal coil 472 and data coil 368B of BTE 342B. Specifically, external data coil assembly 354A is configured such that a sufficient amount of magnetic flux generated thereby is received by both of internal coil 472 and data coil 368B to enable data communication between coil 368A and coils 472, 368B.

The desired configuration of external data coil assembly 354A is provided by physically adjusting one or more elements of external data coil assembly 354A with respect to housing 325A. Specifically, in the embodiments of FIG. 8, one or more elements of external data coil assembly 354A are physically adjusted to orient data coil 368A and thus axis of symmetry 582 to enable the desired inductive coupling between all coils. This orientation of data coil 368A may be substantially similar to the changes discussed above with reference to FIGS. 6B and 6C. As noted, the physical adjustment of one or more components to orient data coil 368A and thus axis of symmetry 582 is described below with reference to FIGS. 13 and 14.

Furthermore, embodiments of the present invention are primarily discussed with reference to an external transmitting data coil assembly having one or more physically adjustable elements. It should be appreciated that in alternative embodiments of the present invention, a one or more elements of a receiving coil assembly, such as an internal coil assembly or the coil assembly of a data receiving BTE may have one or more adjustable elements to alter the inductive coupling between the elements. For example, referring to such embodiments with reference to FIG. 8, one or more elements of external data coil assembly 354B may be adjustable with respect to housing 325B to alter the coupling between data coil assemblies 354A and 354B. In such embodiments, receiving data coil assembly 354B may be adjusted in the manners described above.

Figure 9:
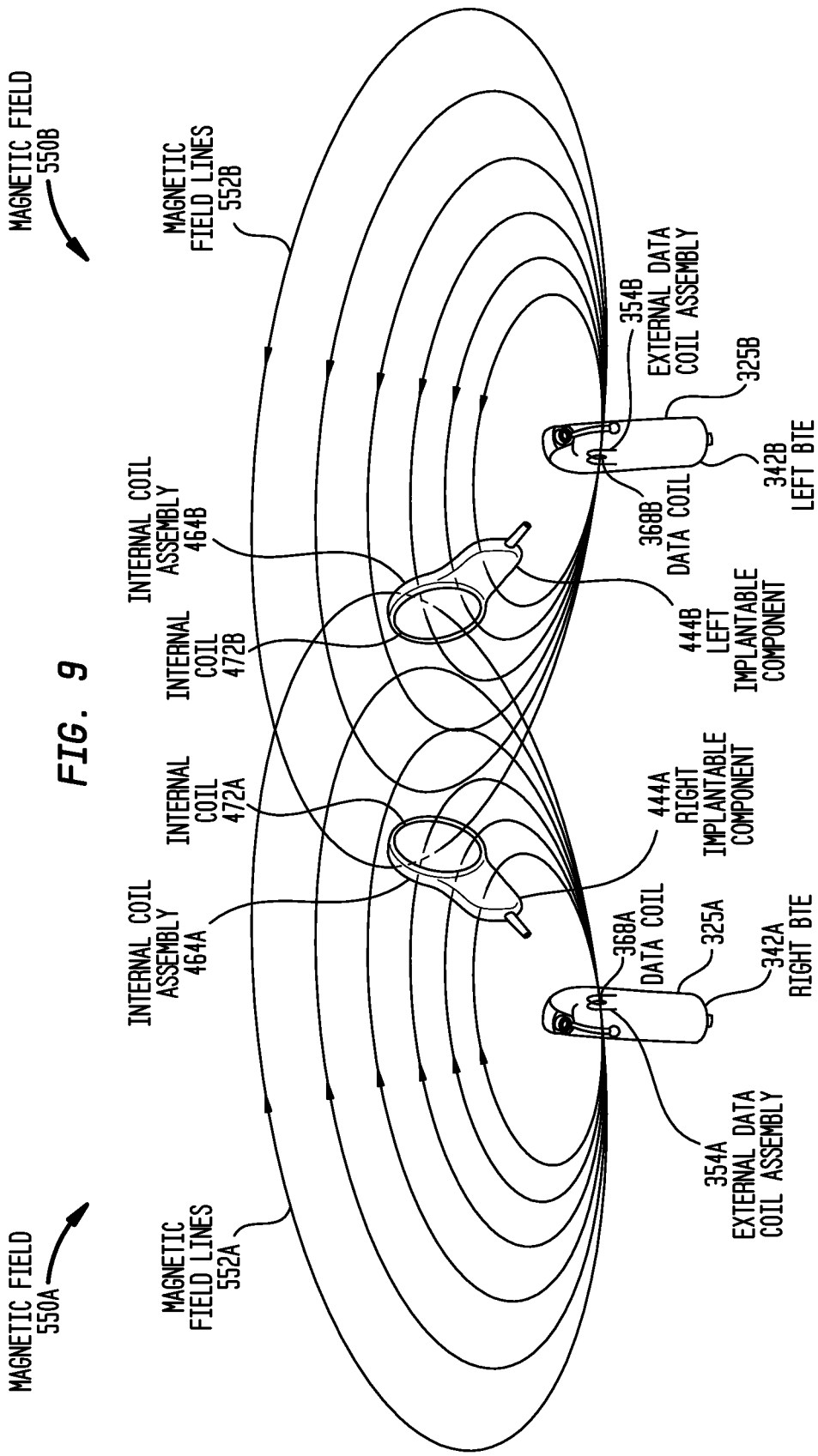
FIG. 9 is a diagram illustrating the inductive coupling between two external components and two implantable components of a cochlear implant, in accordance with embodiments of the present invention.

FIG. 9 is a schematic diagram of a cochlear implant illustrating the inductive coupling in a full bilateral cochlear implant in accordance with embodiments of the present invention. As shown, the cochlear implant comprises a right implant system 920 and a left implant system 922. Right implant system 920 comprises a right BTE 342A configured to be positioned adjacent the recipient's right ear. BTE 342A comprises external data coil assembly 354A having data coil 368A therein. Right implant system 920 further comprises right implantable component 444A positioned near the right side of the recipient's skull. Right implantable component 444A comprises internal coil assembly 464A having internal coil 472A therein.

Left implant system 922 comprises a left BTE 342B configured to be positioned adjacent the recipient's left ear. BTE 342B comprises external data coil assembly 354B having data coil 368B therein. Left implant system 922 further comprises left implantable component 444B positioned near the left side of the recipient's skull. Left implantable component 444B comprises internal coil assembly 464B having internal coil 472B therein.

In the embodiments of the present invention shown in FIG. 9, data coil 368A is configured to inductively transmit data to internal coil 472A and one or more components of left implant system 922. In the specific embodiments shown, data coil 368A is configured to inductively transmit data to internal coil 472B of left implantable component 444B. Thus, external data coil assembly 354A is configured such that a sufficient amount of magnetic flux generated thereby is received by both of internal coil 472A and internal coil 472B to enable data communication between coil 368A and coils 472.

The desired configuration of external data coil assembly 354A is provided by physically adjusting one or more elements of external data coil assembly 354A with respect to housing 325A. Specifically, in the embodiments of FIG. 9, one or more elements of external data coil assembly 354A are physically adjusted to orient data coil 368A to enable the desired inductive coupling between data coil 368A and coils 472. This orientation of data coil 368A may be substantially similar to that discussed above with reference to FIGS. 6B and 6C. As noted, the physical adjustment of one or more components to orient data coil 368A is described below with reference to FIGS. 13 and 14.

Furthermore, in the illustrative embodiments of FIG. 9, data coil 368B is configured to inductively transmit data to internal coil 472B and one or more components of right implant system 920. In the specific embodiments shown, data coil 368B is configured to inductively transmit data to internal coil 472A of right implantable component 444A. Thus, external data coil assembly 354B is configured such that a sufficient amount of magnetic flux generated thereby is received by both of internal coil 472A and internal coil 472B to enable data communication between coil 368A and coils 472.

The desired configuration of external data coil assembly 354B is provided by physically adjusting one or more elements of external data coil assembly 354B. Specifically, in the embodiments of FIG. 9, one or more elements of external data coil assembly 354B are physically adjusted with respect to housing 325B to orient data coil 368B to enable the desired inductive coupling between data coil 368A and coils 472. This orientation of data coil 368B may be substantially similar to that discussed above with reference to FIGS. 6B and 6C. As noted, the physical adjustment of one or more components to orient data coil 368B is described below with reference to FIGS. 13 and 14.

Figure 10:
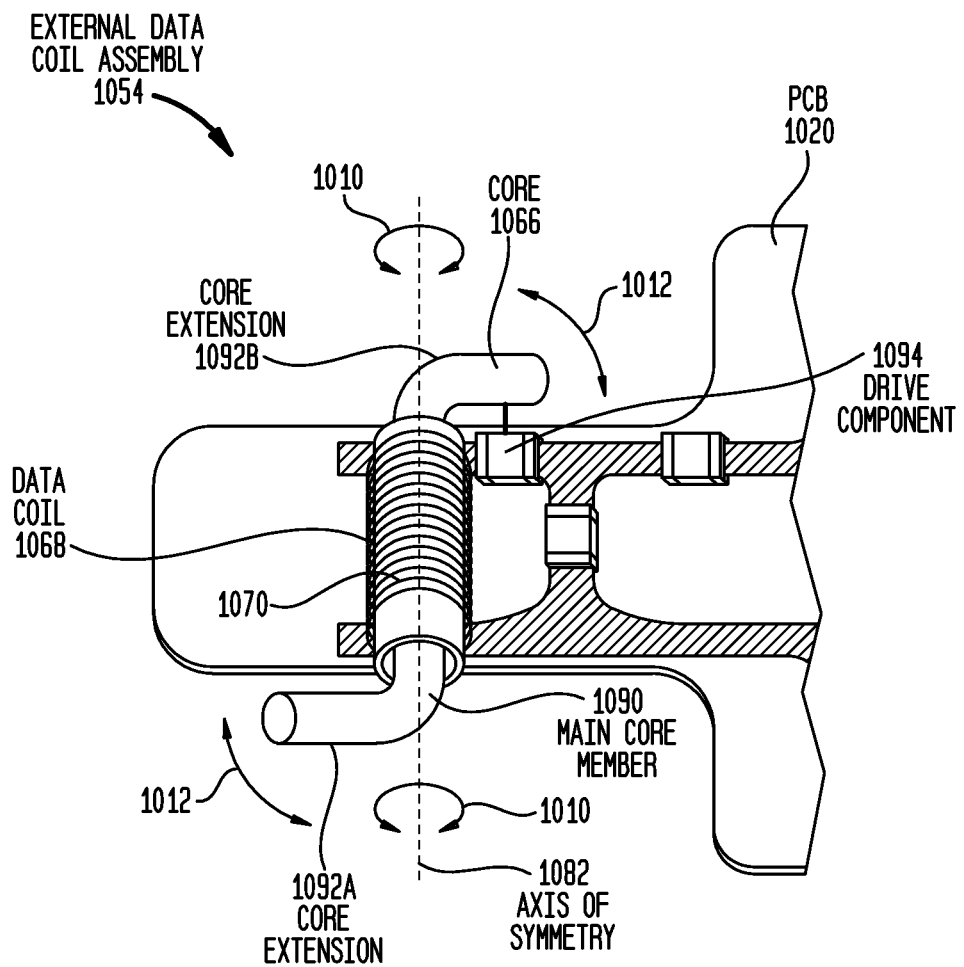
FIG. 10 is a perspective view of an external coil assembly in accordance with embodiments of the present invention.

FIG. 10 is a perspective view of an external coil assembly 1054 in accordance with embodiments of the present invention. In the embodiments of FIG. 10, external coil assembly 1054 is positioned on a printed circuit board (PCB) 1020, and comprises a data coil 1068 and a core 1066.

Data coil 1068 is a wire antenna coil comprised of multiple turns 1070 of electrically insulated single-strand or multi-strand wire affixed to PCB 1020. As would be appreciated, turns 1070 of data coil 1068 may have circular, oval, square or rectangular shapes, and may be wound in a single or multi layered bobbin structure. FIG. 10 illustrates a specific arrangement in which turns 1070 are substantially circular.

Furthermore, as noted above, turns 1070 of data coil 1068 may be wound around an air core, or a material having a higher permeability than air, such as a ferromagnetic material. In the embodiments of FIG. 10, core 1066 comprises a volume of ferromagnetic material having a general S or Z shape. Specifically, core 1066 comprises a cylindrical main member 1090 about which turns 1070 of data coil 1068 are circumferentially positioned. Two substantially perpendicular extensions 1092 extend from main member 1090.

Main core member 1090 is positioned such that a longitudinal axis through the geometric cross-section thereof is coaxial with a longitudinal axis through the geometric center of the area bounded by the turns 1070 of data coil 1068. In other words, main member 1090 has a longitudinal axis that is aligned with axis of symmetry 1082 of data coil 1068.

As noted above, embodiments of the present invention provide the ability to alter the inductive coupling between data coil 1068 and a receiving coil, such as an implanted internal coil discussed above. The inductive coupling between data coil 1068 and a receiving coil is altered by physically adjusting one or more elements of external data coil assembly 1054. Particularly, in the specific embodiments of FIG. 10, core 1066 is physically rotatable about axis of symmetry 1082. The rotation of core 1066 is shown by arrows 1010.

In embodiments of the present invention, the magnetic field generated by external data coil assembly 1054 will vary depending on the rotational position of core 1066. In other words, when core 1066 is in a first position, the generated magnetic field with have magnetic field lines disposed in first locations. However, when core 1066 is rotated to a second rotational position, the generated magnetic field with have magnetic field lines disposed in second locations. Thus, the rotation of core 1066 to a new rotational position results in a change in the flow of magnetic flux within a magnetic field generated by external coil assembly 1054. That is, when external data coil assembly 1054 commences transmission of data with the core in its new rotational position, the flow of magnetic flux within the magnetic field will be different than when the core was in the previous position.

In embodiments of the present invention, core 1066 may be manually rotated by a recipient, clinician or other user. For example, in certain embodiments, a user may have access to core 1066, and a user may adjust core 1066 in the directions shown by arrows 1012. In other embodiments, core 1066 may be connected to one or more components extending outside of the housing in which external data coil assembly 1054 is mounted, and a user may manipulate those components. In still other embodiments, portions of core 1066 may extend from the housing.

In other embodiments, a drive component 1094 is mechanically connected to core 1066. Based on electrical signals received from, for example, a control module, user inputs, etc., drive component 1094 is configured to rotate core 1066 about axis 1082. As would be appreciated, various mechanisms for mechanically rotating core 1066 based on an electrical signal are known in the art, any of which may be used in embodiments of the present invention.

In alternative embodiments of the present invention, the inductive coupling between data coil 1068 and a receiving coil is altered by physically adjusting the position of core 1066 with respect to coil 1068. In these embodiments, the position of core 1066 is adjusted along axis of symmetry 1082 and coil 1068 remains in a fixed position. The translation of core 1066 to a new position with respect to data coil 1068 results in a change in the flow of magnetic flux within a magnetic field generated by external coil assembly 1054. That is, when external data coil assembly 1054 commences transmission of data with the core in its new position, the flow of magnetic flux within the magnetic field will be different than when the core was in the previous position. As noted above, the flow of magnetic flux within a magnetic field may be visualized by the magnetic field lines. Thus, the resulting change in the flow of the magnetic flux may be viewed as a change in the location of the magnetic field lines within the generated field.

Furthermore, FIG. 10 illustrates an embodiment of the present invention in which turns 1070 of data coil 1068 are affixed to PCB 1020 and core 1066 is movable (i.e. rotatable and repositionable) with respect to data coil 1068. It would appreciated that in alternative embodiments, data coil 1068 may be movable with respect to a stationary core 1066 to cause desired changes in the inductive coupling between data coil 1068 and a receiving coil.

Figure 11:
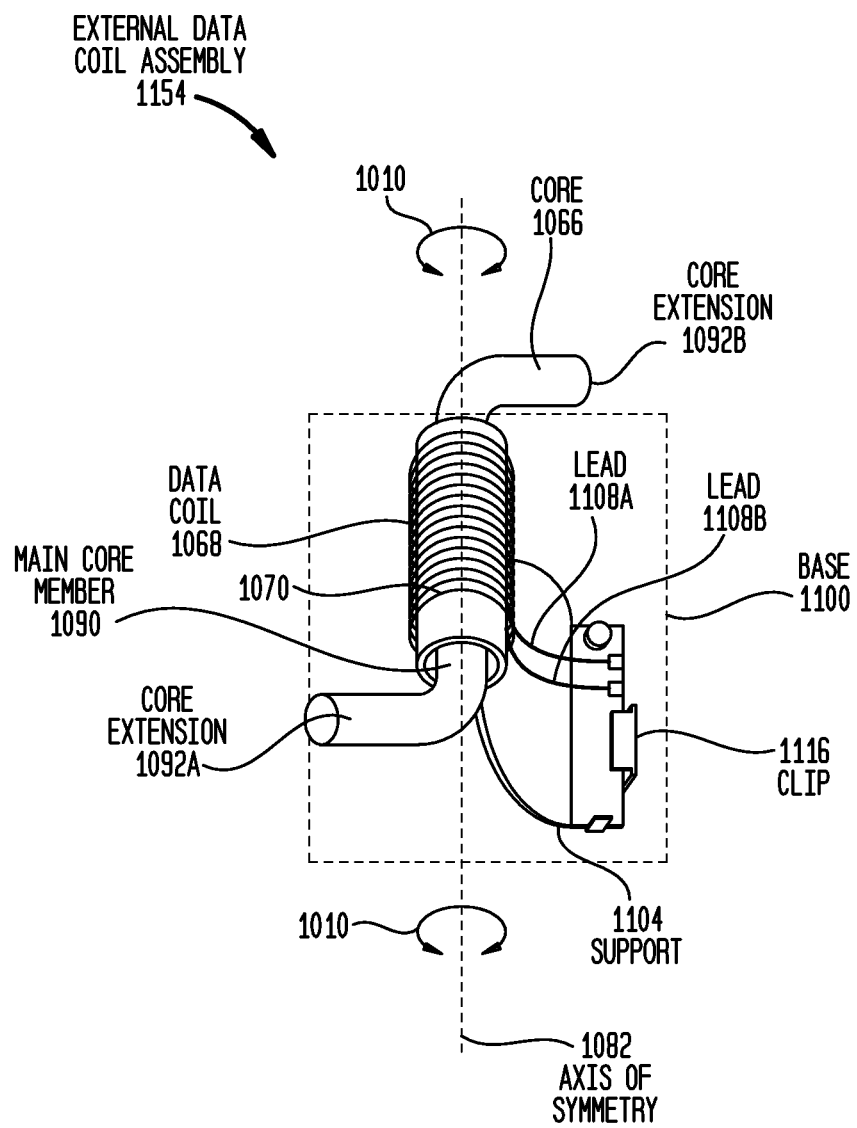
FIG. 11 is a perspective view of an external coil assembly in accordance with embodiments of the present invention.

FIG. 11 is a perspective view of an external coil assembly 1154 in accordance with embodiments of the present invention. External coil assembly 1154 is substantially similar to external coil assembly 1054 of FIG. 10 and comprises a data coil 1068 and a core 1066.

As noted above with reference to FIG. 10, the embodiments of the present invention shown in FIG. 11 provide the ability to alter the inductive coupling between data coil 1068 and a receiving coil, such as an implanted internal coil discussed above. The inductive coupling between data coil 1068 and a receiving coil is altered by physically adjusting one or more elements of external data coil assembly 1054. Particularly, in the specific embodiments of FIG. 11, core 1066 is physically rotatable about axis of symmetry 1082. The rotation of core 1066 is shown by arrows 1010.

In the illustrative embodiments of FIG. 11, external data coil assembly 1154 is connected to a support 1104. Support 1104 is coupled to a base 1100 via a clip 1116. Base 1100 may comprise, for example, a region of a behind-the-ear (BTE) unit. Leads 1108 electrically connect data coil 1068 to a transmitter that operates with external data coil assembly 1154 to transmit data to a receiver coil.

In embodiments of the present invention, support 1104 may be movable relative to base 1100, thereby providing the ability to rotate, translate, reposition etc., the one or more elements of external data coil assembly 1154. These embodiments are detailed below with reference to FIGS. 13 and 14.

Figure 12:
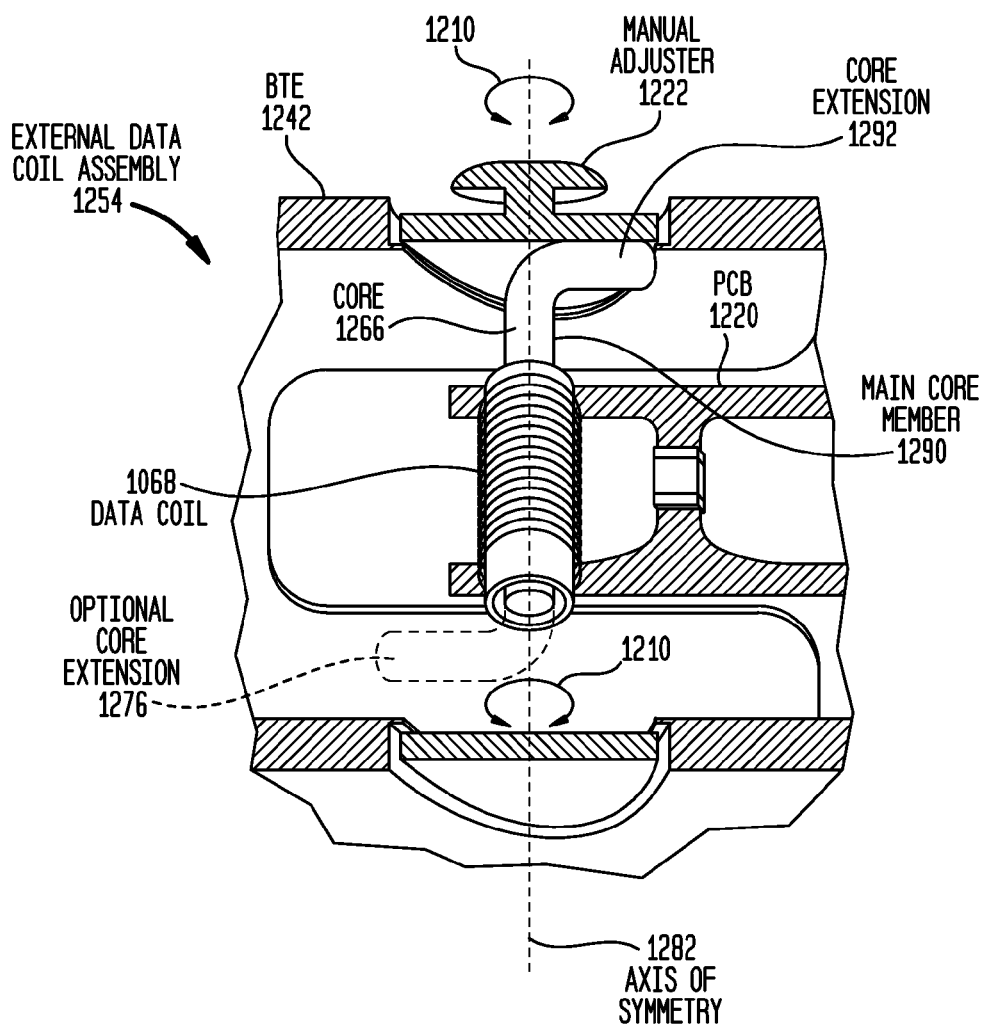
FIG. 12 is a cross-sectional view of an external component of a cochlear implant, in accordance with embodiments of the present invention.

FIG. 12 is a cross-sectional view of a Behind-The-Ear (BTE) unit 1242 of a cochlear implant, in accordance with embodiments of the present invention. As shown, BTE 1242 comprises an external data coil assembly 1254 which is substantially similar to external data coil assembly 1054 of FIG. 10. In particular, external coil assembly 1254 is positioned on a printed circuit board (PCB) 1020, and comprises a data coil 1068. Data coil 1068 is a wire antenna coil comprised of multiple turns 1070 of electrically insulated single-strand or multi-strand wire affixed to PCB 1020.

Furthermore, as noted above, turns 1070 of data coil 1068 may be wound around an air core, or a core 1266 comprising a material having a higher permeability than air, such as a ferromagnetic material. In the embodiments of FIG. 12, core 1266 comprises a volume of ferromagnetic material having a general L-shape. Specifically, core 1266 comprises a cylindrical main member 1290 about which turns 1070 of data coil 1068 are positioned. A substantially perpendicular extension 1292 extends from main member 1290.

Main core member 1290 is positioned such that a longitudinal axis through the geometric cross-section thereof is coaxial with a longitudinal axis through the geometric center of the area bounded by the turns 1070 of data coil 1068. In other words, main member 1090 has a longitudinal axis that is aligned with axis of symmetry 1082 of data coil 1068.

As noted above, embodiments of the present invention provide the ability to alter the inductive coupling between data coil 1068 and a receiving coil, such as an implanted internal coil discussed above. The inductive coupling between data coil 1068 and a receiving coil is altered by physically adjusting one or more elements of external data coil assembly 1254. Particularly, in the specific embodiments of FIG. 12, core 1266 is physically rotatable about axis of symmetry 1082. The rotation of core 1066 is shown by arrows 1010.

As noted above with reference to FIG. 10, the rotation of a core such as core 1266 to a new rotational position results in a change in the flow of magnetic flux within a magnetic field generated by external coil assembly 1254. That is, when external data coil assembly 1254 commences transmission of data with the core in its new rotational position, the flow of magnetic flux within the magnetic field will be different than when the core was in the previous position. As noted above, the flow of magnetic flux within a magnetic field may be visualized by the magnetic field lines. Thus, the resulting change in the flow of the magnetic flux may be viewed as a change in the location of the magnetic field lines within the generated field.

In embodiments of the present invention, core extension 1290 is mechanically coupled to manual adjuster 1222. Manual adjuster 1222 comprises, for example, a knob which is accessible to a recipient, surgeon, clinician or other user of BTE 1242. Using manual adjuster 1222, the user may rotate core about axis of symmetry 1082 in the directions shown by arrows 1210. As would be appreciated one or more stopper or locking mechanisms may be provided to retain core 1266 in a desired orientation.

In certain embodiments of the present invention, core 1266 may comprise an optional core extension 1276. When in use, core extension 1276 converts core 1266 into an S or Z shape, thereby changing the magnetic field pattern generated by external coil assembly 1254. In embodiments of the present invention, a user may determine if the L-shaped or S-shaped is desirable. In these embodiments, core 1266 may be made of a single part or multiple parts, and, if made from multiple parts, each part can have the same or a different magnetic permeability to that of the other part(s). In addition, a small air gap may exist between the parts, for example, between the main member 1290 and the one or more extensions 1292.

Figure 13:
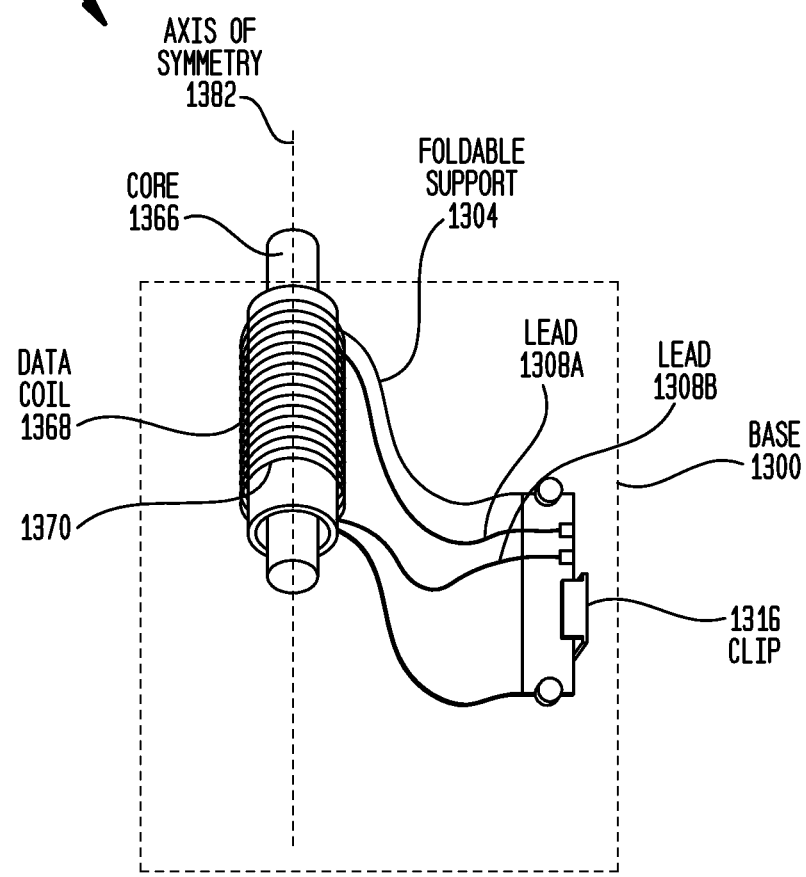
FIG. 13 is a perspective view of an external coil assembly in accordance with embodiments of the present invention.

FIG. 13 is a perspective view of an external coil assembly 1354 in accordance with embodiments of the present invention. In the embodiments of FIG. 13, external data coil assembly 1354 comprises a data coil 1368 and a core 1366. Similar to the embodiments described above, data coil 1368 is a wire antenna coil comprised of multiple turns 1370 of electrically insulated single-strand or multi-strand wire. As would be appreciated, turns 1370 of data coil 1368 may have a variety of shapes. FIG. 13 illustrates a specific arrangement in which turns 1370 are substantially circular.

Also, as noted above, turns 1370 of data coil 1368 may be wound around an air core, or a material having a higher permeability than air, such as a ferromagnetic material. In the embodiments of FIG. 13, turns 1370 are wound about a core 1366 comprising a cylindrical volume of ferromagnetic material. As discussed above, core 1366 may have different shapes in alternative embodiments.

Core 1366 is positioned such that a longitudinal axis through the geometric cross-section thereof is coaxial with a longitudinal axis through the geometric center of the area bounded by the turns 1370 of data coil 1368. In other words, core 1366 has a longitudinal axis that is aligned with axis of symmetry 1382 of data coil 1368.

As noted above, embodiments of the present invention provide the ability to alter the inductive coupling between data coil 1368 and a receiving coil, such as an implanted internal coil discussed above. The inductive coupling between data coil 1368 and a receiving coil is altered by physically adjusting one or more elements of external data coil assembly 1354 relative to the recipient worn housing. Particularly, in the specific embodiments of FIG. 13, the orientation or position of data coil 368 and core 1366 is adjustable. That is, elements of external data coil assembly 1354 are movable with respect to the housing.

The adjustment in the physical location or orientation of the components of external data coil assembly 1354 is provided by foldable support 1304 affixed to the data coil assembly. Support member 1304 is coupled to a base 1300 via a clip 1316. Support 1304 is configured to provide the ability to adjust the location or orientation of data coil 1368. As noted above with reference to FIGS. 6A-6C, a change in the orientation of data coil 1368 refers to a physical adjustment of the coil resulting in a change in the orientation of axis of symmetry 1382. A change in the position of coil 1368 refers to a change in location of the coil with respect to base 1300. For example, a change in position may refer to positioning of one or more portions of coil 1368 closer to, or farther away from, base 1300. Furthermore, a change in position may refer to a lateral movement of data coil 1368 within a plane that is parallel to base 1300.

In the embodiments of FIG. 13, support 1304 comprises a foldable support. In other words, one or more portions of support 1304 are configured to be manually folded or bent to provide the desired change in orientation or position of data coil 1368. In other embodiments, a drive component is provided to bend or fold selected portions of support 1304 based on electrical signals received from, for example, a control module, user inputs, etc. In embodiments of FIG. 13, once a desired orientation or position of data coil 1368 is obtained, support 1304 is configured to retain the coil in the desired orientation/position.

Base 1300 may comprise, for example, a region of a behind-the-ear (BTE) unit. Leads 1308 electrically connect data coil 1368 to a transmitter that operates with external data coil assembly 1354 to transmit data to a receiver coil.

Figure 14:
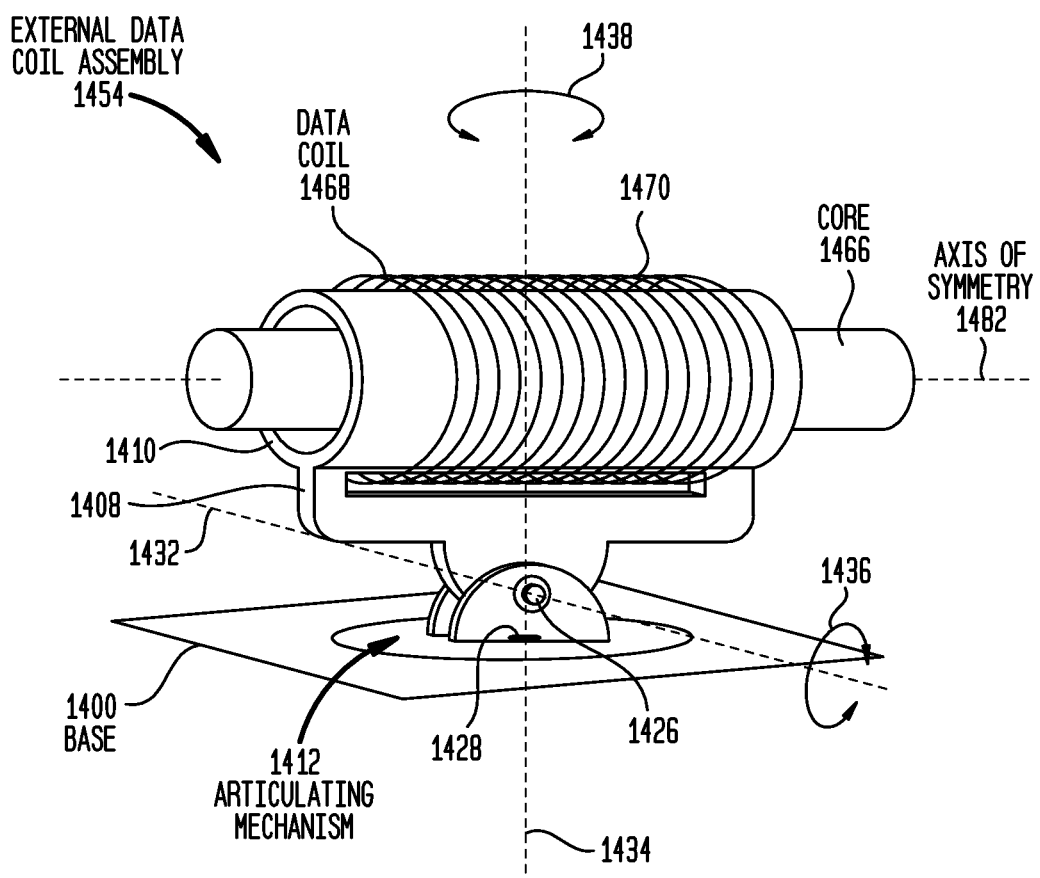
FIG. 14 is a perspective view of an external coil assembly in accordance with embodiments of the present invention.

FIG. 14 is a perspective view of an external data coil assembly 1454 in accordance with embodiments of the present invention. In the embodiments of FIG. 14, external data coil assembly 1454 comprises a data coil 1468 and a core 1466. Similar to the embodiments described above, data coil 1468 is a wire antenna coil comprised of multiple turns 1470 of electrically insulated single-strand or multi-strand wire. As would be appreciated, turns 1470 of data coil 1468 may have a variety of shapes. FIG. 14 illustrates a specific arrangement in which turns 1470 are substantially circular.

Also, as noted above, turns 1470 of data coil 1468 may be wound around an air core, or a material having a higher permeability than air, such as a ferromagnetic material. In the embodiments of FIG. 14, turns 1470 are wound around a core 1466 comprising a cylindrical volume of ferromagnetic material. As discussed above, core 1466 may have different shapes in alternative embodiments.

Core 1466 is positioned such that a longitudinal axis through the geometric cross-section thereof is coaxial with a longitudinal axis through the geometric center of the area bounded by the turns 1470 of data coil 1468. In other words, core 1466 has a longitudinal axis that is aligned with axis of symmetry 1482 of data coil 1468.

As noted above, embodiments of the present invention provide the ability to alter the inductive coupling between data coil 1468 and a receiving coil, such as an implanted internal coil discussed above. The inductive coupling between data coil 1468 and a receiving coil is altered by physically adjusting one or more elements of external data coil assembly 1454. Particularly, in the specific embodiments of FIG. 14, the orientation of data coil 368 is adjustable. As detailed above with reference to FIGS. 6A-6C, a change in the orientation of data coil 1468 will result in a corresponding shift of axis of symmetry 1482. This change in the orientation of axis 1482 affects the orientation of the magnetic field generated by external data coil assembly 1454.

The adjustment in the physical orientation of data coil 1468 is provided by support 1404 comprising an upright member 1408 and articulating mechanism 1412. Upright member 1408 is coupled to a cylindrical element 1410 disposed between turns 1470 and core 1466. One or more of turns 1470 and core 1466 may be releasably or non-releasably coupled to cylindrical element 1410. Upright member 1408 is further connected to articulating mechanism 1412. Articulating mechanism is attached to base 1400. Base 1400 may comprise, for example, a region of a behind-the-ear (BTE) unit housing.

In the embodiments of FIG. 14, articulating mechanism 1412 provides the ability to rotate support member 1404, and thus external coil assembly 1454, about an axis 1438 perpendicular to base 1400 extending through the support member. In particular, articulating mechanism 1412 may rotate through at least 180 degrees about axis 1434 in a plane that is substantially parallel to base member 1400. Rotation of articulating mechanism 1412 about axis 1434 is shown by arrow 1438.

Articulating mechanism 1412 is further configured to rotate about a second axis 1432 parallel to base 1400 extending through the support member. In particular, articulating mechanism 1412 may rotate through at least 180 degrees about axis 1432 in a plane that is substantially perpendicular to base member 1400. Rotation of articulating mechanism 1412 about axis 1434 is shown by arrow 1438.

In embodiments of the present invention, a recipient, surgeon clinician or other user may manually rotate articulating mechanism 1412 about axes 1432, 1434 by manipulating control knobs 1426, 1428 on the articulating mechanism. In alternative embodiments, articulating mechanism 1412 may include, or operate in conjunction with, drive components to rotate the mechanism in response to an electrical signal.

Figure 15:
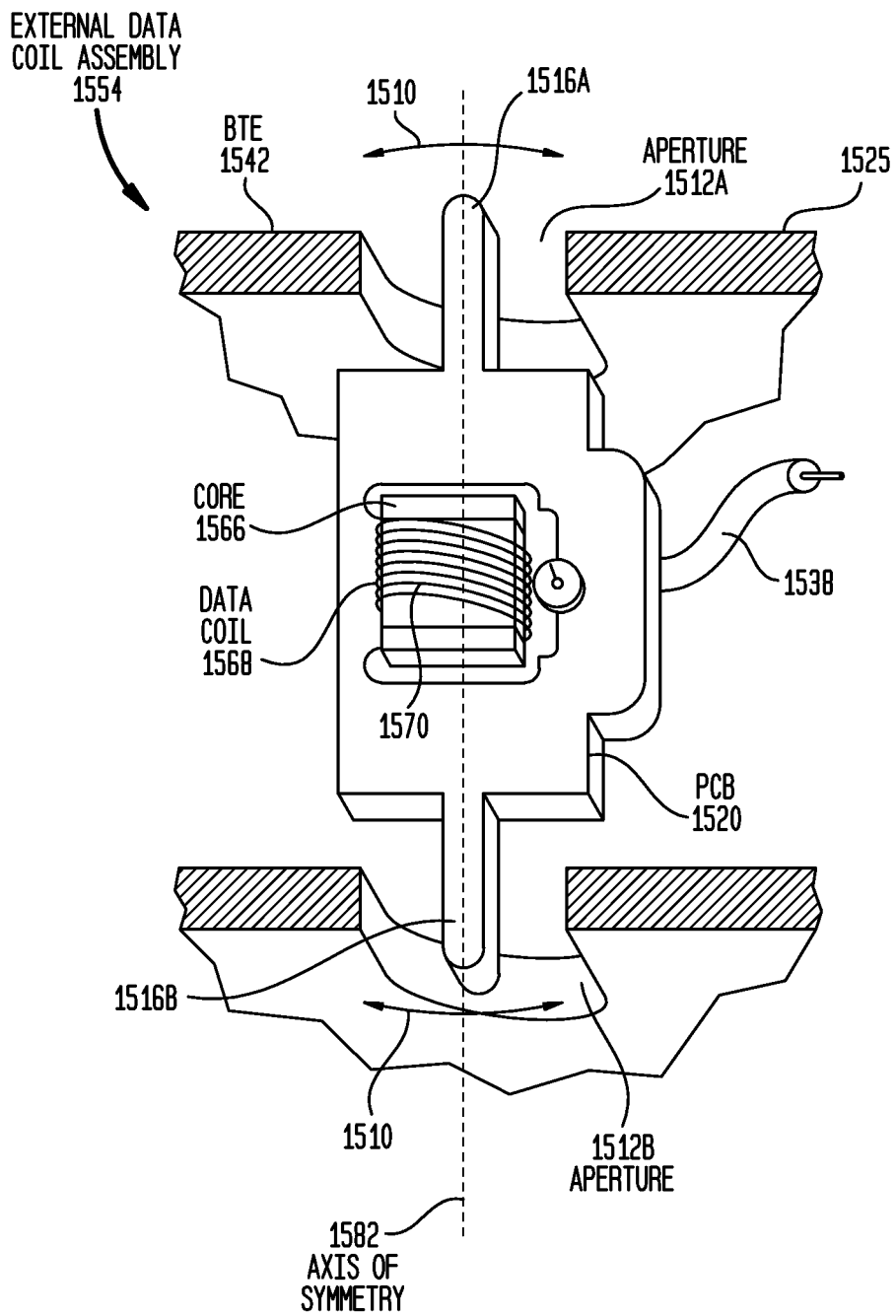
FIG. 15 is a cross-sectional view of an external component of a cochlear implant, in accordance with embodiments of the present invention.

FIG. 15 is a cross-sectional view of behind-the-ear (BTE) unit 1542 of a cochlear implant, in accordance with embodiments of the present invention. As shown, BTE 1542 comprises an external data coil assembly 1554 surface mounted to a printed circuit board (PCB) 1520 positioned in a housing 1525. External data coil assembly 1554 comprises a data coil 1568 and a core 1566.

Data coil 1068 is a wire antenna coil comprised of multiple turns 1570 of electrically insulated single-strand or multi-strand wire. As would be appreciated, turns 1570 of data coil 1568 may have circular, oval, square or rectangular shapes, and may be wound in a single or multi layered bobbin structure. FIG. 15 illustrates a specific arrangement in which turns 1570 have an oval shape.

Furthermore, as noted above, turns 1570 of data coil 1568 may be wound around an air core, or a material having a higher permeability than air, such as a ferromagnetic material. In the embodiments of FIG. 15, core 1566 comprises a rectangular volume of ferromagnetic material.

Core 1566 is positioned such that a longitudinal axis through the geometric cross-section thereof is coaxial with a longitudinal axis through the geometric center of the area bounded by the turns 1570 of data coil 1568. In other words, core 1566 has a longitudinal axis that is aligned with axis of symmetry 1582 of data coil 1568.

As noted above, embodiments of the present invention provide the ability to alter the inductive coupling between data coil 1568 and a receiving coil, such as an implanted internal coil discussed above. The inductive coupling between data coil 1568 and a receiving coil is altered by physically adjusting one or more elements of external data coil assembly 1554 with respect to housing 1525. Particularly, in the specific embodiments of FIG. 15, extensions 1516 of PCB 1520, to which external data coil assembly 1554 is coupled, extend outside of BTE 1542 through apertures 1512. A user is able to manually adjust the location or orientation of PCB 1520 using exposed extensions 1516. For example, in certain embodiments, PCB 1520 is mounted on a pivot element (not shown) or a semi-rigid holder 1538, and a user may actuate extensions 1516 in the directions indicated by arrows 1510.

FIG. 16 is a flowchart illustrating a method 1600 performed in accordance with operations embodiments of the present invention. As shown, method 1600 begins at block 1602 where an external housing worn by a recipient having a data coil assembly positioned therein, and an internal coil assembly implanted in the recipient is provided. The housing may comprise a behind-the-ear (BTE) unit positioned on the recipient's ear. The data coil assembly is configured to be inductively coupled to the internal coil assembly. As would be appreciated, internal coil assembly may be provided through surgical implantation, and the data coil assembly may be provided by a clinician, audiologist, etc., following the surgery.

At block 1604, an indication of the strength of the inductive coupling between the data coil assembly and the internal coil assembly is received. As previously noted, magnetic flux is generated by the data coil assembly and is received by the internal coil. The more magnetic flux that reaches the internal coil, the better or stronger the coupling between the data coil and the internal coil. The coupling strength between the coils may be expressed by a coupling factor R. The coupling factor is a value between zero and one. A coupling factor of 1 indicates a perfect coupling between the coils (i.e. all flux generated by the external data coil assembly is received by the internal coil and thus the strongest possible coupling), while a coupling factor of zero indicates that the coils are independent (i.e. no magnet flux generated by the external data coil assembly is received by the internal coil and thus the weakest possible coupling).

In certain embodiments, indication of the strength of the coupling is generated automatically and received by the hearing prosthesis. For example, the prosthesis may be configured to automatically determine that an undesirable inductive coupling exists between two components and, as described below, to adjust the coupling accordingly. In other embodiments, the indication is generated in response to a user input. For example, the user may determine that an inductive coupling is undesirable and provide an appropriate indication that is received by the prosthesis for adjustment. In still other embodiments, the indication of the strength of the coupling is generated by the prosthesis, fitting system, etc., and is received by the clinician, audiologist, or other user. In these embodiments, the indication may comprise, for example, an audible or visual indication. Visual indications may be provided by, for example, Light Emitting Diodes (LEDs), LCD display, graphical user interface, etc.

At block 1606, one or more elements of data coil assembly are physically adjusted, with respect to the housing, to alter the inductive coupling between the data coil assembly and the implanted coil assembly. The physical adjustment of the one or more components may occur in accordance with the embodiments described above.

Furthermore, embodiments of the present invention have been primarily discussed with reference to an external transmitting data coil assembly having one or more physically adjustable elements. It should be appreciated that in alternative embodiments of the present invention, a one or more elements of a receiving coil assembly, such as an internal coil assembly or the coil assembly of a data receiving BTE may have one or more adjustable elements to alter the inductive coupling between the elements.

As one of ordinary skill in the art would appreciate, implantable medical devices envisaged by the present invention include, but are not limited to, cochlear implants, nerve stimulators, pace makers, glucose meters, and any other type of implantable medical device requiring wireless communication.

For example, embodiments of the present invention may be implemented in an active medical device. An active medical is any medical device relying for its functioning on a source of electrical energy or any source of power other than that directly generated by the human body or by gravity. An active implantable medical device (AIMD) is any active medical device which is intended to be totally or partially introduced, surgically or medically, into the human body or by medical intervention into a natural orifice, and which is intended to temporarily or permanently remain in the patient after the procedure.

As noted above, embodiments of the present invention have been primarily described above with reference to adjusting one or more elements of a data coil assembly to enable data communication between the data coil assembly and desired receiving coils. This typically includes configuring the data coil assembly so that sufficient magnetic flux is received by the desired receiving coils (i.e. increase the inductive coupling between the coils). In specific embodiments of the present invention, the one or more elements of the data coil assembly may be adjusted to lower the inductive coupling between the coils. In such embodiments, it may be desirable to lower the inductive coupling to avoid saturating the receiving coil or as a result of limitations of the dynamic input range of the receiver.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A hearing prosthesis comprising:
an internal coil assembly implantable in a recipient; and
an external data coil assembly positioned in a housing worn by the recipient, wherein the data coil assembly is configured to be inductively coupled to the internal coil assembly in order to transcutaneously transfer data to the internal coil assembly,
wherein one or more elements of the data coil assembly are physically adjustable with respect to the housing to alter the inductive coupling.

2. The hearing prosthesis of claim 1, wherein the one or more adjustable elements of the data coil assembly comprise a wire coil, and wherein at least one of the orientation and the position of the coil is adjustable with respect to the housing to alter the coupling.

3. The hearing prosthesis of claim 2, wherein the data coil assembly is attached to the housing by a support member, and wherein the support member is configured to rotate about at least one axis to change the orientation of the coil.

4. The hearing prosthesis of claim 3, wherein the support member is configured to be rotated manually.

5. The hearing prosthesis of claim 3, further comprises a drive component configured to rotate the support member about the at least one axis in response to a received electrical signal.

6. The hearing prosthesis of claim 1, wherein the one or more adjustable elements of the data coil assembly comprise an elongate core and a wire coil wound around the elongate core, and wherein the core is physically rotatable about a longitudinal axis of the core from a first rotational position to a second rotational position, and wherein the inductive coupling between the data coil assembly and the internal coil assembly is different when the core is in the first and second rotational positions.

7. The hearing prosthesis of claim 6, wherein the core is manually rotatable about the longitudinal axis.

8. The hearing prosthesis of claim 6, further comprising a drive component configured to rotate the core about the longitudinal axis in response to an electrical signal.

9. The hearing prosthesis of claim 1, wherein the data coil assembly comprises a wire coil wound around an elongate core, and wherein the physical location of the core with respect to the housing is adjustable to alter the inductive coupling.

10. The hearing prosthesis of claim 1, wherein the data coil assembly comprises a wire coil wound around an elongate core having a cylindrical main member and one or more cylindrical extensions extending perpendicularly from the main member.

11. The hearing prosthesis of claim 1, wherein the implantable component is configured to transcutaneously transfer data to the external component via the inductive coupling.

12. A transcutaneous energy transfer system for an implantable medical device, comprising:
   an internal coil assembly implantable in a recipient; and
   an external data coil assembly positioned in a housing worn by the recipient and configured to be inductively coupled to the internal coil assembly to transcutaneously transfer data to the internal coil assembly,
   wherein one or more elements of the data coil assembly are physically adjustable with respect to the housing to alter the inductive coupling.

13. The system of claim 12, wherein the one or more adjustable elements of the data coil assembly comprise a wire coil, and wherein at least one of the orientation and position of the coil is adjustable with respect to the housing to alter the coupling.

14. The system of claim 13, wherein the data coil assembly is attached to the housing by a support member configured to rotate about at least one axis to change the orientation of the coil.

15. The system of claim 14, wherein the support member is configured to be rotated manually.

16. The system of claim 14, wherein the support member further comprises a drive component configured to rotate the support member about the at least one axis in response to an electrical signal.

17. The system of claim 12, wherein the one or more adjustable elements of the data coil assembly comprise an elongate core and a wire coil wound around the elongate core, and wherein the core is physically rotatable about a longitudinal axis of the core from a first rotational position to a second rotational position, and wherein the inductive coupling between the data coil assembly and the internal coil assembly is different when the core is in the first and second rotational positions.

18. The system of claim 17, wherein the core is manually rotatable about the longitudinal axis.

19. The system of claim 17, where the support member further comprises a drive component configured to rotate the support member about the at least one axis in response to an electrical signal.

20. The system of claim 12, wherein the data coil assembly comprises a wire coil wound around an elongate core, and wherein the physical location of the core with respect to the coil is adjustable to alter the inductive coupling.

21. The system of claim 12, wherein the data coil assembly comprises a wire coil wound around an elongate core having a cylindrical main member and one or more cylindrical extensions extending perpendicularly from the main member.

22. The system of claim 12, wherein the internal coil assembly is configured to transcutaneously transfer data to the external coil assembly.

23. A method for using a hearing prosthesis comprising an internal coil assembly implantable in a recipient, and an external data coil assembly positioned in a housing worn by the recipient and configured to be inductively coupled to the internal coil assembly, the method comprising:
   receiving an indication of the strength of the inductive coupling between the data coil assembly and the internal coil assembly; and
   physically adjusting one or more elements of the data coil assembly with respect to the housing to alter the inductive coupling between the data coil assembly and the internal coil assembly.

24. The method of claim 23, wherein the data coil assembly comprises a wire coil, and wherein physically adjusting the one or more elements of the data coil assembly comprises:
   adjusting the orientation of the coil with respect to the housing.

25. The method of claim 24, wherein the data coil assembly is attached to a housing of the external component by a support member, and wherein physically adjusting the one or more elements of the data coil assembly comprises:
   rotating the support member about at least one axis.

26. The method of claim 23, wherein the data coil assembly comprises a wire coil wound around an elongate core physically rotatable about a longitudinal axis of the core from a first rotational position to a second rotational position, and wherein physically adjusting the one or more elements of the data coil assembly comprises:
   rotating the coil from the first position to the second position.

27. The method of claim 23, wherein the data coil assembly comprises a wire coil wound around an elongate core, and wherein physically adjusting the one or more elements of the data coil assembly comprises:
   changing the physical location of the core with respect to the housing.

* * * * *